US010932674B2

United States Patent
Luxon et al.

(10) Patent No.: US 10,932,674 B2
(45) Date of Patent: Mar. 2, 2021

(54) DEVICES AND METHODS FOR MONITORING PHYSIOLOGIC PARAMETERS

(71) Applicant: Respirix, Inc., San Francisco, CA (US)

(72) Inventors: Evan S. Luxon, Omaha, NE (US); Daniel R. Burnett, San Francisco, CA (US); Stephen Boyd, San Francisco, CA (US)

(73) Assignee: Respirix, Inc., San Francisco, CA (US)

( * ) Notice: Subject to any disclaimer, the term of this patent is extended or adjusted under 35 U.S.C. 154(b) by 217 days.

(21) Appl. No.: 15/582,227

(22) Filed: Apr. 28, 2017

(65) Prior Publication Data

US 2017/0238815 A1    Aug. 24, 2017

Related U.S. Application Data

(63) Continuation of application No. PCT/US2015/059608, filed on Nov. 6, 2015.
(Continued)

(51) Int. Cl.
*A61B 5/0205* (2006.01)
*A61B 5/029* (2006.01)
(Continued)

(52) U.S. Cl.
CPC ........ *A61B 5/02055* (2013.01); *A61B 5/0002* (2013.01); *A61B 5/021* (2013.01); *A61B 5/024* (2013.01); *A61B 5/0205* (2013.01); *A61B 5/02007* (2013.01); *A61B 5/029* (2013.01); *A61B 5/02405* (2013.01); *A61B 5/0402* (2013.01); *A61B 5/087* (2013.01); *A61B 5/486* (2013.01); *A61B 5/4875* (2013.01);
(Continued)

(58) Field of Classification Search
None
See application file for complete search history.

(56) References Cited

U.S. PATENT DOCUMENTS 4,762,130 A    8/1988  Fogarty et al.
5,188,618 A    2/1993  Thomas
(Continued)

FOREIGN PATENT DOCUMENTS

| JP | 2010-213773 | 9/2010 |
| WO | WO 2007/092052 | 12/2007 |
| WO | WO 2013/179181 | 12/2013 |

OTHER PUBLICATIONS

Tusman, "Pulmonary blood flow generates cardiogenic oscillations", Respiratory Physiology & Neurobiology 167(3);247-54—May 2009.
(Continued)

*Primary Examiner* — Michael R Bloch
(74) *Attorney, Agent, or Firm* — Levine Bagade Han LLP

(57) ABSTRACT

Devices and methods for monitoring physiologic parameters are described herein which may utilize a non-invasive respiratory monitor to detect minor variations in expiratory airflow pressure known as cardiogenic oscillations which are generated by changes in the pulmonary blood volume that correspond with the cardiac cycle. These cardiogenic oscillations are a direct indicator of cardiac function and may be used to correlate various physiologic parameters such as stroke volume, pulmonary artery pressure, etc.

39 Claims, 18 Drawing Sheets

Related U.S. Application Data

(60) Provisional application No. 62/076,603, filed on Nov. 7, 2014, provisional application No. 62/107,443, filed on Jan. 25, 2015, provisional application No. 62/145,919, filed on Apr. 10, 2015.

(51) Int. Cl.

| | | |
|---|---|---|
| *A61B 5/00* | (2006.01) | |
| *A61B 5/087* | (2006.01) | |
| *A61B 5/024* | (2006.01) | |
| *A61B 5/02* | (2006.01) | |
| *A61B 5/021* | (2006.01) | |
| *A61B 5/0402* | (2006.01) | |
| *A61B 5/08* | (2006.01) | |
| *A61B 5/091* | (2006.01) | |
| *A61B 5/097* | (2006.01) | |

(52) U.S. Cl.
CPC ............ *A61B 5/682* (2013.01); *A61B 5/7246* (2013.01); *A61B 5/7278* (2013.01); *A61B 5/082* (2013.01); *A61B 5/0816* (2013.01); *A61B 5/0878* (2013.01); *A61B 5/091* (2013.01); *A61B 5/097* (2013.01)

(56) References Cited

U.S. PATENT DOCUMENTS

| | | |
|---|---|---|
| 5,704,345 A | 1/1998 | Berthon-Jones |
| 5,803,066 A | 9/1998 | Rapoport et al. |
| 6,029,665 A | 2/2000 | Berthon-Jones |
| 6,186,956 B1* | 2/2001 | McNamee ............. A61B 5/083 600/526 |
| 6,238,349 B1 | 5/2001 | Hickey |
| 6,428,483 B1 | 8/2002 | Carlebach |
| 6,654,631 B1 | 11/2003 | Sahai |
| 6,675,797 B1 | 1/2004 | Berthon-Jones |
| 6,733,464 B2 | 5/2004 | Olbrich et al. |
| 6,739,335 B1 | 5/2004 | Rapport et al. |
| 7,077,810 B2 | 7/2006 | Lange et al. |
| 7,282,032 B2 | 10/2007 | Miller |
| 7,320,320 B2 | 1/2008 | Berthon-Jones |
| 7,730,886 B2 | 6/2010 | Berthon-Jones |
| 7,740,591 B1 | 6/2010 | Starr et al. |
| 8,343,057 B2 | 1/2013 | Starr et al. |
| 8,343,064 B2 | 1/2013 | Bardy |
| 8,360,060 B2 | 1/2013 | Berthon-Jones |
| 8,381,722 B2 | 2/2013 | Berthon-Jones |
| 8,424,527 B1 | 4/2013 | Kayyali et al. |
| 8,644,915 B2 | 2/2014 | Chou |
| 8,794,236 B2 | 8/2014 | Phuah et al. |
| 8,831,715 B2 | 9/2014 | Boege et al. |
| 9,026,190 B2 | 5/2015 | Shenasa et al. |
| 9,220,856 B2 | 12/2015 | Martin et al. |
| 9,549,678 B2 | 1/2017 | Silber |
| 2006/0047210 A1 | 3/2006 | Moroki et al. |
| 2006/0287621 A1 | 12/2006 | Atkinson et al. |
| 2007/0032733 A1* | 2/2007 | Burton ............... A61B 5/02405 600/509 |
| 2007/0270699 A1 | 11/2007 | Crabtree et al. |
| 2007/0299354 A1* | 12/2007 | Striepe ............... A61B 5/02405 600/509 |
| 2010/0036266 A1 | 2/2010 | Myklebust et al. |
| 2010/0094270 A1 | 4/2010 | Sharma |
| 2010/0099993 A1* | 4/2010 | Cohen ................ A61B 5/02028 600/485 |
| 2011/0015496 A1 | 1/2011 | Sherman et al. |
| 2011/0245691 A1 | 10/2011 | Silber |
| 2012/0059340 A1 | 3/2012 | Larsson |
| 2013/0066166 A1 | 3/2013 | Burnett et al. |
| 2013/0066225 A1 | 3/2013 | Kojouri |
| 2013/0296837 A1 | 11/2013 | Burnett et al. |
| 2013/0331724 A1* | 12/2013 | Altobelli ................ A61B 5/082 600/532 |
| 2014/0107404 A1 | 4/2014 | Gruber |
| 2014/0155764 A1 | 6/2014 | Silber |
| 2014/0228657 A1 | 8/2014 | Palley et al. |
| 2014/0228781 A1 | 8/2014 | Boyle et al. |
| 2014/0275857 A1* | 9/2014 | Toth ...................... A61B 5/087 600/301 |
| 2014/0276120 A1 | 9/2014 | Starr et al. |
| 2015/0018660 A1 | 1/2015 | Thomson et al. |
| 2015/0182713 A1 | 7/2015 | Phuah et al. |
| 2016/0067433 A1 | 3/2016 | Martin et al. |

OTHER PUBLICATIONS

Gesche et al. "Continuous blood pressure measurement by using the pulse transit time: comparison to a cuff-based method." (2011).

Tusman et al, "Pulmonary blood flow generates cardiogenic oscillations", Respiratory Physiology & Neurobiology 167(3):247-54 • May 2009.

Young et al. "Noninvasive Monitoring Cardiac Output Using Partial CO2 Rebreathing." Critical Care Clinic (2010): 383-392.

* cited by examiner

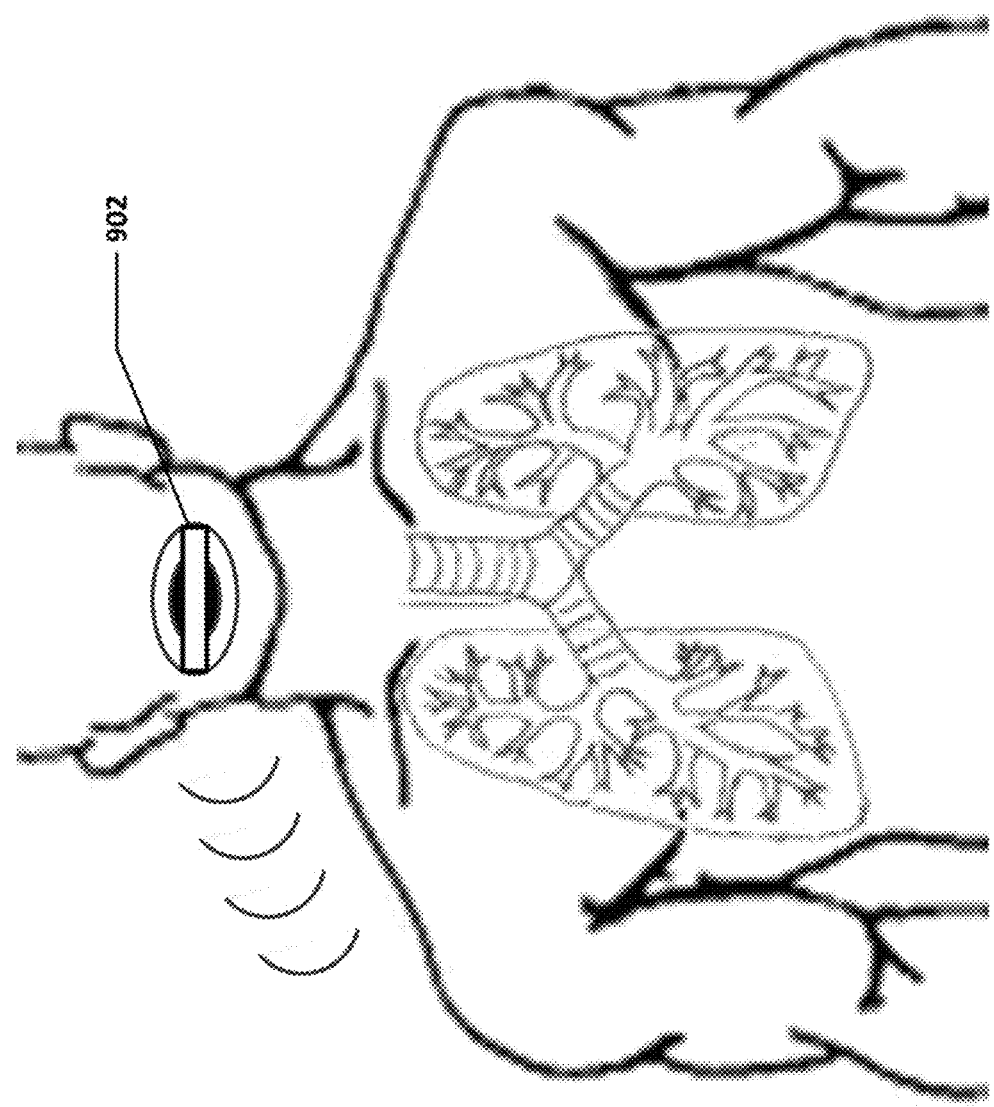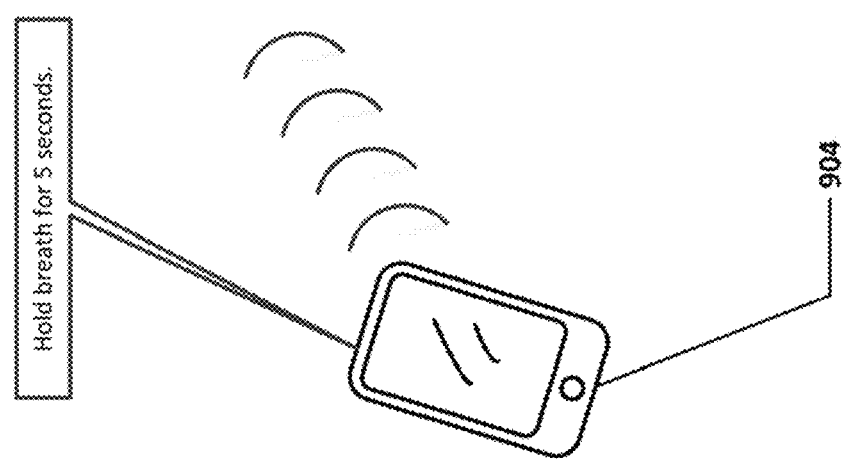
FIG. 9

DEVICES AND METHODS FOR MONITORING PHYSIOLOGIC PARAMETERS

CROSS-REFERENCE TO RELATED APPLICATIONS

This application is a continuation of International Application No. PCT/US2015/059608 filed Nov. 6, 2015, which claims the benefit of priority to U.S. Provisional Application No. 62/076,603 filed Nov. 7, 2014 and U.S. Provisional Application No. 62/107,443 filed Jan. 25, 2015 and U.S. Provisional Application No. 62/145,919 filed Apr. 10, 2015, each of which is incorporated herein by reference in its entirety.

FIELD OF THE INVENTION

The present invention relates to the field of monitoring cardiac function.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Heart failure (HF) is the leading cause of hospitalization among adults over 65 years of age in the United States. In 2014, more than 5.1 million people in the United States were living with a diagnosis of HF, and as many as one in nine deaths each year can be attributed to complications stemming from this disease. Acute decompensation is a life-threatening consequence of HF that occurs when uncontrolled fluid retention in the thoracic cavity prevents the heart from maintaining adequate circulation. An important component of managing HF patients is maintaining an appropriate fluid volume by adjusting the patient's medications in response to his/her cardiac function. Fluid volume metrics, such as dyspnea, edema, and weight gain, can be monitored by patients at home as an indirect indicator of worsening cardiac function, but are highly non-specific and cannot predict decompensation risk with sufficient resolution to affect the hospitalization rate. Recent evidence has shown that directly monitoring cardiac function via an implantable sensor can provide clinicians with a remote monitoring tool to determine when medication adjustments can prevent decompensation and the need for hospitalization. However, the cost and invasive nature of these sensors severely restrict their potential for clinical adoption.

Various mechanisms have been employed to determine cardiac function and health. These include invasive technologies such as the Swan Ganz catheter and a pulmonary artery implant to less invasive technologies such as arterial waveform monitoring devices, and surface worn technologies such as bioimpedance monitors and noncontact technologies such as scales to monitor weight. The invasive technologies are more accurate but also more risky while the noninvasive technologies have less risk but are more cumbersome and typically less accurate. The presence of collected fluid, peripheral edema, ascites, pleural effusions and weight can also be used to monitor cardiac function in CHF patients, but these parameters are merely symptomatic surrogates with poor correlation to actual cardiac output.

What is needed is a simple, repeatable, accurate monitor of cardiac function and other physiologic parameters that allows consistent measurement of cardiac output in the clinic, hospital and/or home environment. The present invention provides an easy to use, home-based device and method for the tracking of cardiac output, stroke volume and cardiac function. The invention can also be used for monitoring mechanical phases of the cardiac cycle, which are useful for diagnosing structural issues such as heart valve pathologies.

SUMMARY OF THE INVENTION

The present invention is a non-invasive respiratory monitor that is capable of directly monitoring cardiac function in a remote setting. The respiratory monitor, or airway device/controller, detects minor variations in expiratory airflow pressure known as cardiogenic oscillations, which are generated by changes in the pulmonary blood volume that correspond with the cardiac cycle. The strength, or magnitude, of cardiac oscillations is a direct indicator of cardiac function and is directly correlated with stroke volume and inversely proportional to pulmonary artery pressure.

In one example of a system which may be used for determining one or more physiologic parameters of a subject, the system may generally comprise a flow or pressure sensor configured to monitor respiratory activity of the subject, a controller in communication with the flow or pressure sensor, wherein the controller is programmed to: extract one or more cardiogenic oscillation waveforms from the respiratory activity, determine shape data of the cardiogenic oscillation waveforms to determine one or more physiologic parameters of the subject, provide an indication of a health status of the subject, and prompt the subject to actively modify their respiratory activity, if needed, to reduce or enhance an effect of respiratory activity on the cardiogenic oscillation waveforms.

In use, one example of how such a system may be used for determining one or more physiologic parameters of a subject may generally comprise receiving flow or pressure data related to respiratory activity of the subject, extracting one or more cardiogenic oscillation waveforms from the flow or pressure data, determining shape data of the one or more cardiogenic oscillation waveforms, determining one or more physiologic parameters based on the determined shape data, providing a health status to the subject based on the determined one or more physiologic parameters, and prompting the subject to actively modify their respiratory activity, if needed, to reduce or enhance an effect of respiratory activity on the cardiogenic oscillation waveforms.

Minor, cyclic waveforms caused by cardiogenic oscillations, or cardiac pulses, can be detected in the bulk pressure and flow measurements of expiration and inspiration. The method and device of the present invention utilizes this ability to detect and isolate cardiac oscillations, or pulsations, within the sensed pressure profile in the airway of an animal or human. Pressure measured at around 100 Hz, or around 80 Hz to around 120 Hz, within the airway of a subject allows for excellent resolution of the pressure signal. When pressure in the airway is measured at this frequency, cardiogenic oscillations may be visible in the resulting pressure curve. These pulsations are best seen at end expiration, or during a breath hold, but can be seen throughout the breathing cycle. This result may be the result of the heart beating in close proximity to the lungs, which subsequently transmits the pressure fluctuations through the trachea to the mouth and nose. It may also be the result of pulmonary blood flow, which may slightly compress the lungs as the heart beats.

Cardiogenic oscillations also occur in other measurements of the breath, such as CO2 concentration and temperature. Although the preferred embodiment makes use of pressure and flow measurements, the same analyses and diagnoses described herein may be made using cardiogenic oscillations in other parameters.

The magnitude of cardiac oscillations may be indicated by the standard deviation, or variations, of the cardiac oscillation pressure waveform and is a direct indicator of cardiac function and is directly correlated with stroke volume and inversely proportional to pulmonary artery pressure. The magnitude of cardiac oscillations may also be indicated by the peak-to-peak amplitude or the area under the carve of the waveform. The cardiac performance of patients with heart failure is reduced when compared to that of healthy individuals, which will dampen the cardiac oscillation curve relative to healthy subjects.

The present invention senses pressure and/or flow within the airway by exposing the airway (via the patient's nose or mouth) to one or more pressure, flow, and/or other sensor(s). When the epiglottis is opened, this exposure to the airway allows pressure and/or flow sensors to detect small pulsations that occur during heart function. These fluctuations may also be detected with a sensitive enough sensor, when the epiglottis is closed. With an appropriately sensitive sensor sampling at a rapid frequency, waveforms can be seen in the airway corresponding to contractions, relaxation and valve openings in the heart. This phenomenon has been found to be repeatable and allows not only for tracking of heart and lung function and/or conditions (i.e. pulmonary edema, pleural effusions, congestive heart failure, aortic insufficiency, mitral, pulmonic, tricuspid insufficiency, etc.) but can be used to diagnose disease in patients using the airway device. Whereas ECG is used to monitor and diagnosis heart conditions based on the electrical signal being sent to the heart, the present invention provides additional information based on the actual mechanical function of the heart.

Preferably, the amplitude and/or area under the curves for pressure and flow data can be used to determine relative pulmonary blood flow, relative stroke volume, and/or relative pulmonary artery pressure. For example, as pulmonary blood flow increases, the amplitudes of the flow pulsations in the breath increase. Additional parameters, such as the slope of the pressure curve, changes in the curve or standard deviation of the curve can also be used to determine relative cardiac function. When tracked over time, these parameters provide noninvasive insights into the patient's changing cardiac health and can be used to adjust his/her care accordingly. This is particularly useful for people who are being monitored regularly for changes in their conditions, such as patients with heart failure. Patient pressure/flow curve data can also be compared to those of healthy or unhealthy patient populations to asses a particular patient's, or a group of patients', health.

In its preferred embodiment the patient is prompted by a controller to breathe into the device naturally for several cycles. This may be done automatically by a controller. Further, the airway device may be simply placed in the mouth and worn while going about activities of daily living to allow for natural sensing of respiratory rate, another powerful predictor and indicator of progressing illness. In some embodiments, the airway device/controller can calculate the rate of exhalation and capture cardiogenic oscillations at the same phase of breathing for each patient to allow for consistent measures of cardiac output and lung function. In other embodiments, the mean or median of the samples may be used as the representative value for that particular measurement. For example, the patient may breath regularly for 2, 5, or 10 minutes, during which the pressure, flow, and other signals are captured, and at the end the of the session values such as the average amplitude of the signal caused by cardiogenic oscillations may be reported. In this way intra-measurement variability is reduced and the signal-to-noise ratio is improved.

Further, in some embodiments, the patient may be prompted by a controller to inhale deeply and hold his/her breath (or, if used in conjunction with a ventilator, the ventilator can be paused at end inhalation, end exhalation, or elsewhere, either manually or, preferably, automatically with communication between airway device/controller and the ventilator or incorporation of airway device/controller into the ventilator) to see the impact of breathing on the pressure waveform. Variability in the respiratory pulse pressure waveform can be used to determine hydration status, as well as volume status. Dehydrated or hypovolemic, patients will see a pulse pressure waveform that varies throughout the respiratory cycle due to the change in cardiac function with the changing thoracic pressures found with respiration. As fluid status is restored, this variability is reduced and lack of variability can provide a powerful indicator that fluid status has been restored. In addition to pulse pressure variability, heart rate variability may also be used to assess fluid status. Variability may be assessed on a continuous basis during natural or mechanical ventilation or may be assessed during a respirator pause to look for changes at end-inspiration and/or end-expiration over time to track variability. The ratio of end-inspiratory to end-expiratory pulse amplitude during respiration or with a breath hold may be determined. Variations in waveform peak-to-peak period and magnitude, in addition to other parameters, may be determined.

A respiratory pause may also be used to provide another determinant of cardiac output-change in end-tidal CO2 after a respirator pause. The use of respiratory pulse pressure waveform analysis in conjunction with the end tidal CO2 method may improve the accuracy of the results and make this method less susceptible to pulse pressure variability.

In addition, actual, or absolute, cardiac output can be determined without calibration using the airway device/controller. By combining the airway device controller with spirometry or a ventilator, the volume of air in the lung can be accurately estimated. In addition, actual, or absolute, cardiac output can be determined using a CO2 sensor to determine end tidal CO2, as well as an air flow sensor and oxygen sensor. The calculations to determine cardiac output can be performed as described in "Noninvasive Monitoring Cardiac Output Using Partial CO2 Rebreathing" by Brian P. Young, MD, and Lewis L. Low, MD. A spirometer and/or ventilator may be stationary or ambulatory, or may be miniature and built into the mouthpiece itself.

In another embodiment, absolute stroke volume, cardiac output, and/or pulmonary artery pressure can be estimated by comparing the amplitude of the pressure or flow curves in the airway to the volume of air in the lungs and using correlation coefficients based on patient based variables such as their gender and height, in a similar manner to the way correlation coefficients can be use with pulse-transit-time to estimate blood pressure (see Gesche, Heiko, et al. "Continuous blood pressure measurement by using the pulse transit time: comparison to a cuff-based method." (2011)). In this manner, the present invention may be used to estimate the actual volume displaced in the lung by the cardiac pulse, which represents the true stroke volume. An ECG or pulse oximetry signal may be used to help determine the pulse transit time.

Furthermore, in the setting of low pulse pressure variability this technique can also be used to calculate the dead space in the lung. This can be done by comparing the cardiac pulse pressure waveform at end-inhalation and end-exhalation. If tidal volume is known (i.e. with spirometry or mechanical ventilation), then, assuming the cardiac pulse is a constant, one can calculate the dead space in the lung by looking at the magnitude. If the cardiac pressure pulse and calculating the predicted amplitude of the cardiac pulse, measuring the actual amplitude of the cardiac pulse, and determining the dead space information from the difference between the two (due to the extra dead space being compressed also). Total lung volume may also be calculated by the application of a fixed amount of analyte or a small bolus of gas/air to the lung then calculating the resulting concentration of the analyte or the final pressure after delivery of the bolus of air (assuming a breath hold at end-inspiration).

Due to its ease of use and non-invasive nature, the present invention lends itself well to home healthcare monitoring. In a preferred embodiment, the airway device will be handheld or body worn (but does not need to be). The airway device may continuously or intermittently measure flow rates/volumes, pressure, temperature, and/or gas concentrations in the airway. Patient manipulations may be requested by the airway device/controller (i.e. "Breathe deep then hold your breath for 5 seconds") and the airway device/controller may be able to automatically or manually communicate the extracted information to the patient and/or healthcare provider, or with a mobile device, computer, server or other device. Alerts may be programmed into the airway device and/or controller, as well, to warn of impending issues or danger, or to guide the user through its use. By continuously sensing the pressure, the airway device/controller may also provide continuous feedback on the adequacy of the patient manipulations (i.e. "Slow down the speed of your breath") to optimize the patient manipulations for improved data capture. Feedback and alerts may be audible, visual, vibration, etc. Alerts may also be sent to a physician, monitor, hospital, EMR etc. Alerts may be transferred wirelessly to any device including a mobile device, computer, server, etc.

In temperature-sensing embodiments, the airway device/controller may sense inhaled and exhaled temperature and the controller, based on flow/heat exchange algorithms, reports the patient's temperature. Alternatively, the airway device/controller may report trends in temperature based on baseline data acquired when the patient was at a normal temperature. This deviation from baseline data can be utilized with any of the sensed parameters thereby allowing for the determination of a relative change in any of the parameters without knowing the actual value of any of the parameters.

In any of the home health, clinic or hospital embodiment of the airway device/controller of present invention, additional functionality may be incorporated, including temperature sensing, respiratory function monitoring (i.e. spirometry), acoustic monitoring (to track wheezing in asthmatics, etc.), detection of analytes and/or compounds in the breath (i.e. urea, markers of infection, $O_2$, $CO_2$, water vapor, etc.), detection of analytes in the saliva (since the device may be placed inside the mouth in some embodiments). Additional air sensors may include alcohol, and/or other drugs such as narcotics, marijuana, tobacco, etc.

In addition, physical sensors in contact with the body, for example the lips, may include ECG sensors, pulse sensors, mucosal contact sensors, etc. When ECG sensors are in place, sampling of the pulsatile signals in the breath from the cardiogenic oscillations may be syncronized with the ECG signal in order to identify periodic signals, evaluate only the relevant portions of the signal and to reduce the amount of noise. For example, the magnitude of change in the pressure and/or flow signals during a set amount of time (such as 200 or 500 ms) may be the variable of interest that is tracked over time to monitor the cardiac health of the patient. A 2-lead ECG may also be used. The R wave, of the ECCE signal may be used for synchronization. Pulse oximetry may also be used.

The amplitude of cardiac oscillations is directly affected by pulmonary blood flow (PBF) in a linear manner, and the amplitude of this cardiac oscillation peak is likely correlated to the pulmonary blood volume variation (PBVV), which is defined as the change in the pulmonary blood volume from systole to diastole. PBVV has previously been investigated as a metric of cardiac function during heart failure. The PBVV reflects an increase in capillary volume that impinges upon the compliant bronchiole network leading, to the alveoli of the lung and generates high frequency peaks in airway pressure during systole phase of the cardiac cycle. These peaks of cardiac oscillations can be detected. PBVV is proportional to the stroke volume and both values decrease as the cardiac output declines during heart failure. PBVV is also inversely proportional to increases in vascular resistance coincident with heart failure, which restrict the ability of the pulmonary capillaries to expand into the pulmonary airways and contribute to pulmonary hypertension. Thus, the standard deviation of cardiac oscillations (SDCOS) is directly proportional to cardiac output and inversely proportional to pulmonary artery pressure (PAP):

$$SDCOS \propto a*(-\Delta PAP)+b*\Delta PBF$$

where a and b are constants representing compliance of the pulmonary arteries, and bronchioles, respectively.

Pulmonary Arterial Compliance

Pulmonary Arterial Compliance (PAC) is related to Cardiac Heart Failure (CHF) and is a strong indicator of CHF. As the pulmonary artery becomes congested. PAP increases, as PAP increases, the pulmonary artery stretches. But, at higher pressures (above about 25 mmHg), the pulmonary artery becomes less able to stretch further which leads to increased pulse pressure within the pulmonary artery (pulmonary artery pulse pressure, or PAPP). As a result of the higher pressures within the pulmonary artery, more work is required from the right ventricle, and stroke volume (SV) is increased.

PAC Can be Calculated as SV/PAPP (mL/mmHg)

Pulmonary arterial compliance has been shown to be a strong indicator of cardiovascular death or complications. As PAC decreases, the chance of cardiovascular complications or death increases. In addition, treatments for heart failure have been shown to increase the PAC. Currently, the only reliable way to measure PAC is with an invasive catheterization procedure.

Cardiogenic oscillations are generated by the cardiac pulsation in the pulmonary vasculature and are directly related to PAC. As heart failure worsens, stroke volume may decrease which leads to a decrease in the PAC amplitude. Also, PAP increases, the pulmonary artery stiffens, and PAPP increases, also leading to a decrease in the PAC amplitude. A decrease in PAC or PAC amplitude, is a strong indicator of worsening heart health. Amplitude in this instance refers to peak-to-peak amplitude of the curve.

In one use case example, the airway device/controller can be used to track a patient with congestive heart failure. If the patient using the airway device/controller is found to have decreased stoke volume or increased pulmonary artery pressure (via the pressure and/or flow sensors), decreased lung volume and/or decreased respiratory compliance due to fluid accumulation in the pleura and/or pulmonary spaces (via spirometer or pressure sensor) and/or enlargement of the heart, increased pathologic lung sounds (via the acoustic sensor/microphone), increased end-tidal $CO_2$ and/or an increased respiratory rate (via the pressure sensor or spirometer) then the healthcare provider or patient may be alerted that their condition is worsening.

In the home healthcare embodiment, the patient may then be sent home with a networked device (or return to the clinic) for repeat measurements. In the instance where this device is used in combination with daily weighings on a networked scale (the preferred embodiment for congestive heart failure), the airway device/controller may communicate with an existing network provided by the scale or other in-home patient monitoring device, or any network, to alert the user and/or healthcare provider. In this way, the patient's cardiac health can be monitored remotely and noninvasily. This technique may also be used in lieu of radiographic examination to look for pneumo- or hero-thorax following a procedure. Tension pneumothorax and detection of any other lung pathology may be accomplished with this technology, as well, in the hospital, office, or home setting.

In an alternative embodiment, the airway device/controller may record noises directly within the respiratory tract. In this embodiment, the airway device/controller may incorporate a disposable or reusable microphone attached to the ventilator, vent tube or endotracheal tube which can track respiratory sounds and rapidly report the onset of respiratory distress, pneumonia, rales, rhonchi or other changes in lungs sounds. In its preferred embodiment the airway device/controller may incorporate noise cancellation functions. In one such embodiment, two microphones may be used within the airway device with one microphone facing the airway and the other microphone in a similar position within the airway device but sealed off from the airway. The signal from the sealed off microphone may then be subtracted from the microphone open to the airway thereby cancelling out ambient noise and allowing resolution of the physiologic sounds (cardiac, respiratory, gastrointestinal, etc.).

In some embodiments, the airway device/controller could be used in the placement and/or continuous monitoring of an endotracheal tube (ET). ET placement is related to causes of infection in ventilator-acquired pneumonia patients: poor placement can lead to pooling of fluid and, within the fluid, bacterial colonization can occur which then can migrate through the ET or around the cuff of the ET and into the lungs. Pooling of fluid and/or changes in respiratory flow/pressure can be monitored to obtain an early onset indication of infection. Bacteria may also be detected through sensors on the device.

In yet another embodiment, the airway device/controller can detect pathologic behavior of the heart valves. For example, when used in combination with an ECG, the expected mechanical heart behavior and timing of the cardiac cycle is known. By comparing the electrical and mechanical signals, improper mechanical function can be detected, such as the timing of the contraction of the atria or ventricles and opening or closing of the heart valves. Furthermore, the intensity and timing of these signals can also be used to diagnosis pathologies—for example, whether certain phases of the cardiac cycle are prolonged or incomplete, such as with mitral valve regurgitation. This information may be used alone or in combination with the sound information described above or with any other technique for diagnosing heart murmurs in order to better understand the underlying heart function or dysfunction.

This and any of the embodiments described herein may be utilized in a continuous or intermittent manner. The airway device may be designed to be worn by the user or require additional equipment to function and may be applied to the nose and/or mouth or applied directly to an endotracheal tube. The airway device/controller and any or all of its functions may be used in any setting including: the home, office, clinic, hospital ward, ASC or ICU.

The airway device/controller may be used to monitor chronic conditions and/or detect acute conditions including: COPD, asthma, CHF, cancer, stroke, pulmonary embolism, and any other condition that could have an impact on respiratory rate, temperature, stroke volume, heart rate, tidal volume, lung sounds, heart sounds, GI sounds, $pO_2$, $CO_2$, pH, or any other of the monitored parameters.

The airway device may incorporate a controller to analyze the signals from the various sensors. Alternatively, all, or part, of a controller may exist separately from the airway device and communicate with the airway device either wirelessly (via Internet, intranet, WAN, LAN or other network, or it may be local via Bluetooth, Wi-Fi, etc.) or wired. If the connection is wired, it may be continuous or intermittent. For example, the data from the airway device may be periodically transmitted via a USB connection or other type of connection after data has been collected. A wireless connection may also be continuous or intermittent. The controller may be, or communicate with, one or more mobile devices, computers, servers, etc.

BRIEF DESCRIPTION OF THE DRAWINGS

FIG. 9 shows an embodiment of the airway device used wirelessly with a controller in the form of a smart phone.

DETAILED DESCRIPTION OF THE INVENTION

Figure 1:
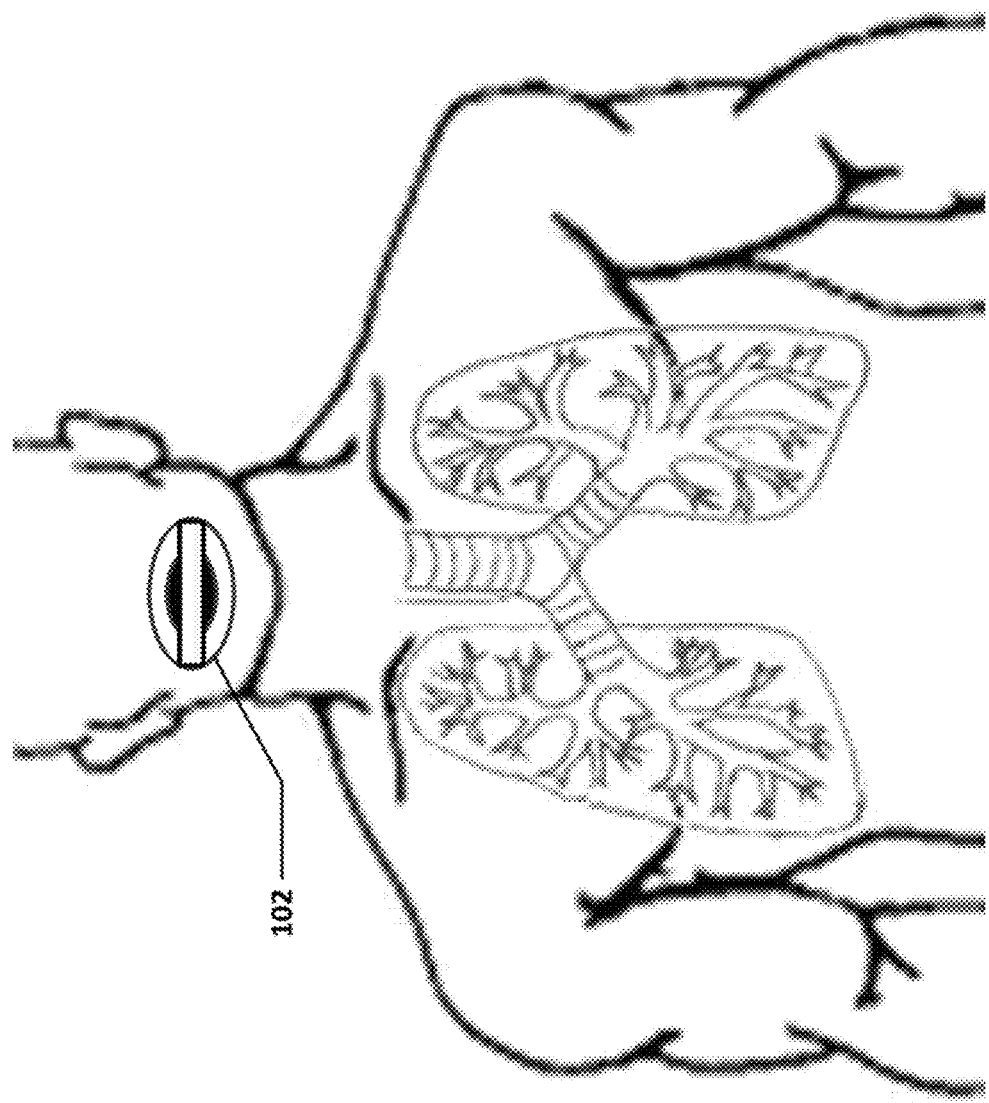
FIG. 1 shows one embodiment of the airway device/controller.

FIG. 1 shows an embodiment of the airway device worn in the mouth of a patient. One of the advantages of a portable embodiment, such as this one, is that it can be worn by a subject that is not only awake and not intubated, but upright and active. In other words, the use of the airway device is not limited to patients on a ventilator or other stationary medical device. The airway device/controller may be used on a patient/user with no additional ventilation support, or airway pressure support. Said another way, the airway device/controller may be used on a patient without a ventilator or CPAP machine or additional flow source, or any sort of artificial ventilation or airway pressure support. The airway device/controller may be used by patients/users who are breathing naturally or normally, or may be used in a "prompt mode", where the controller prompts the user to do something other than breathe naturally. For example, the controller may prompt the user to hold his/her breath, hold his/her breath after inhalation, hold his/her breath after exhalation, hold his/her breath "now", etc.

The airway device 102 contains one or more sensors which can measure and/or calculate airway pressure, airway flow, temperature, sounds, respiratory rate, stroke volume, heart rate, tidal volume, lung sounds, heart sounds, GI sounds, pO2, pCO2, pH, ECG, pulse rate, pulse pressure, spirometry, analytes and/or compounds in the breath (i.e. urea, markers of infection, O2, CO2, urea, water vapor, alcohol, drugs, etc.) or analytes and/or compounds in the saliva, such as glucose, etc.

A controller is either incorporated into the airway device or a separate device which communicates with the airway device either wirelessly or via a wired connection. The controller may be incorporated into a ventilator, a stand-alone device or incorporated into, or in communication with, a computer and/or smartphone.

In a preferred embodiment, the controller is incorporated into a smartphone which communicates wirelessly with the airway device, either on a continuous or intermittent basis. Data transferred from the controller may also be transmitted to from a remote server, for example, via the internet or an intranet. Data from the controller may also be anonymized. Anonymized data may be aggregated across patients for trends analysis. Data collected may include metadata such as patient ID, timestamp, patient medical history, such as weight, medications, etc. Use of the term "airway device" herein may include a controller component.

The airway device may have a portion within the mouth or be completely external. It may also be over the nose either instead of, or in addition to, the mouth. The airway device may purposefully block the nose. The airway device may also be incorporated into an endotracheal tube.

Figure 2:
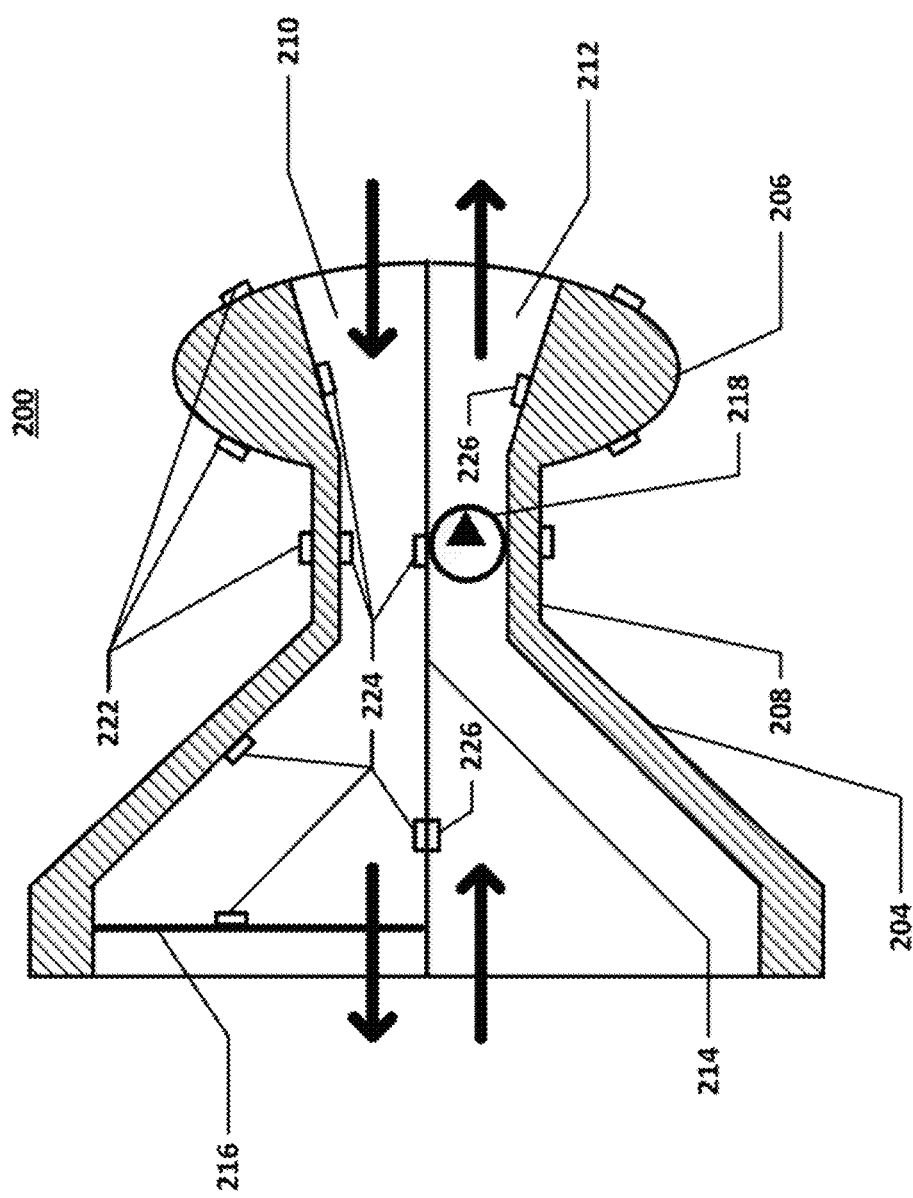
FIG. 2 shows an embodiment of the airway device/controller.

FIG. 2 shows a detailed view of an embodiment of airway device 200. This embodiment includes external opening section 204, mouthpiece section 206 and neck section 208. The mouthpiece device includes at least two airway lumens, exhalation airway lumen 210 and inhalation airway lumen 212. In this embodiment, the two lumens are separated lay divider 214. Alternatively, only one lumen may be present.

Gas outflow vent 216, in the exhalation airway lumen, may include a spirometry function. The vent may also maintain or cause to be maintained a slight positive pressure so that the airway of the subject remains open during breathing, which aids in the ability to sense certain parameters.

The air inflow, or inhalation airway lumen, and/or the exhalation airway lumen, may include one-way 218 valve to help direct exhaled air through the exhalation airway lumen during breathing.

Sensors 222, 224, and 226 may sense any of the parameters listed herewithin. Sensors may be placed in the exhalation airway lumen 210, the inhalation airway lumen 212, or on the outside of the airway device. Sensors 222 on the outside of the device will generally be for contact sensing with the mucosa and/or the lips, such as ECG sensors. Sensors 224 in the exhalation airway lumen may measure parameters associated with exhaled air, including pressure, flow, sounds, temperature, O2, CO2, urea, water vapor, alcohol, drugs, etc. Sensors 226 in the inhalation airway lumen may measure parameters associated with inhaled air, including O2, CO2, urea, water vapor, alcohol, drugs, etc.

Generally, the sensors can be placed anywhere along the length of the airway device, but there may be advantages to certain locations for certain types of sensors. For example, sensors for temperature, water vapor, alcohol, drugs etc. measured in exhaled air, would likely be better placed closer to the subject.

Flow and/or pressure sensors can be placed anywhere along the length of the airway device, but there may be an advantage to placing these sensors in a narrow and/or constant diameter section of the airway device such as within neck 208. A sensor or sensors may also be placed on gas outflow vent 216.

A single use barrier may be used to cover mouthpiece section 206 to maintain sterility of the airway device. Alternatively, a disposable mouthpiece section may be attached to the airway device and removed after use. A heat-moisture exchanger may be used to prevent humidity from the breath entering into the device. Alternatively, the airway device may be sterilizeable or disposable.

Airway device 202 may incorporate hardware and/or software to either act as a controller, or communicate with a controller. The airway device may also act as a "partial controller", where some of the controller activities take place within the airway device, and some take place within a separate controller device.

Airway device may be made out of an suitable material or materials, including polymer, metal, or any other material or any combination of materials. Airway device is preferably relatively light and portable.

Flow/pressure sensors may include orifice plates, cone devices, Pitot tubes, Venturi tubes, flow nozzles, Fleisch or Lilly type pneumotachometers, or any other suitable technology. Sensor resolution is generally high. Pressure sensor range may be around 1.4 E-4 mmHg. Pressure sensor range may be around 1.9 mmHg.

Figure 3:
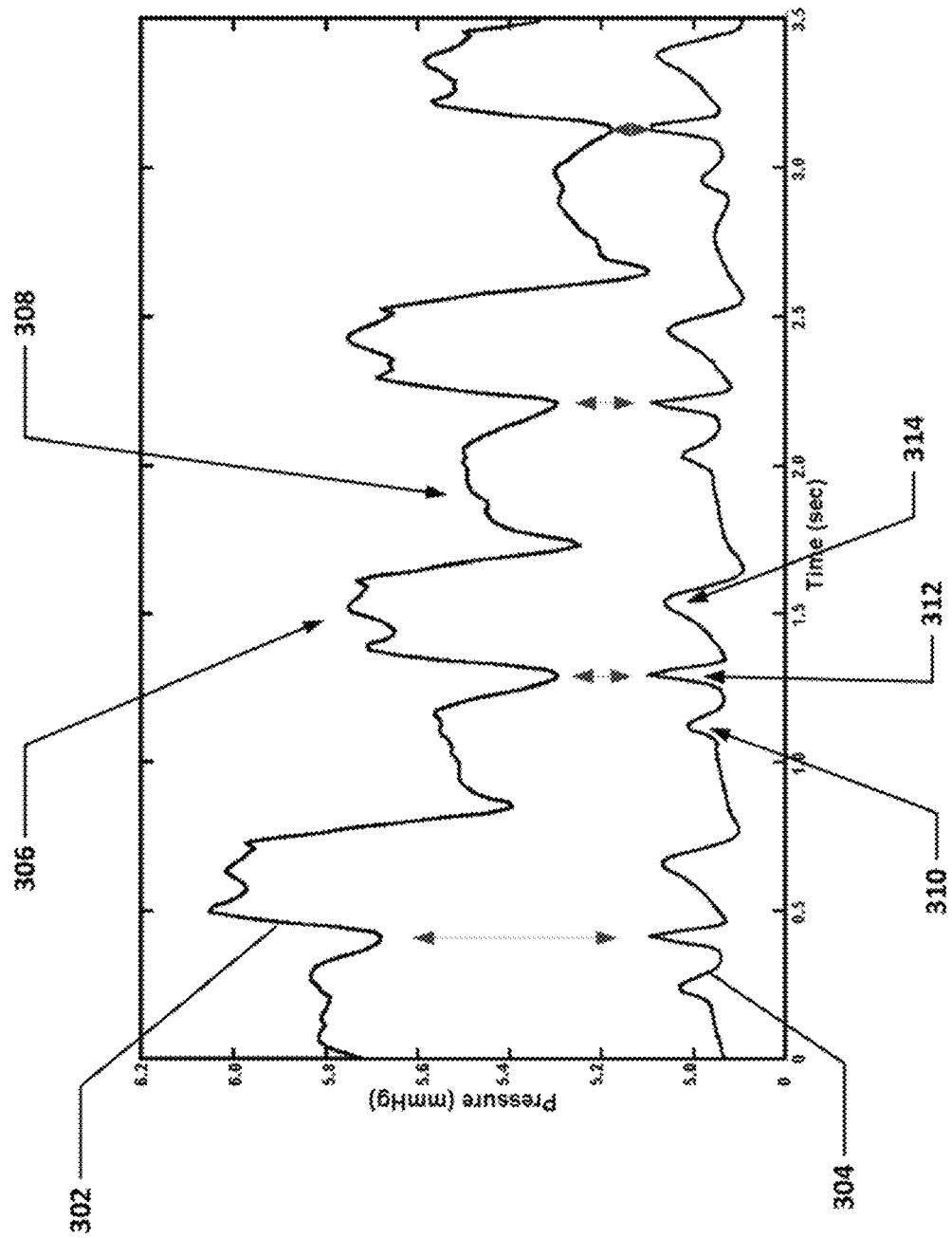
FIG. 3 is a graph showing an ECG overlaid on airway pressure data.

FIG. 3 shows a graph of an ECG along with simultaneously measured airway pressure data. ECG data 304 is shown below airway pressure data 302. Within the airway pressure, systolic pulse data 306 and diastolic pulse data 308 are clearly visible. Within the 3-lead ECG data, P wave 310, QRS complex 312, and T wave 314 are all visible. The dotted arrows show where the QRS complex peak lines up with the valleys of the pressure data.

Figure 4:
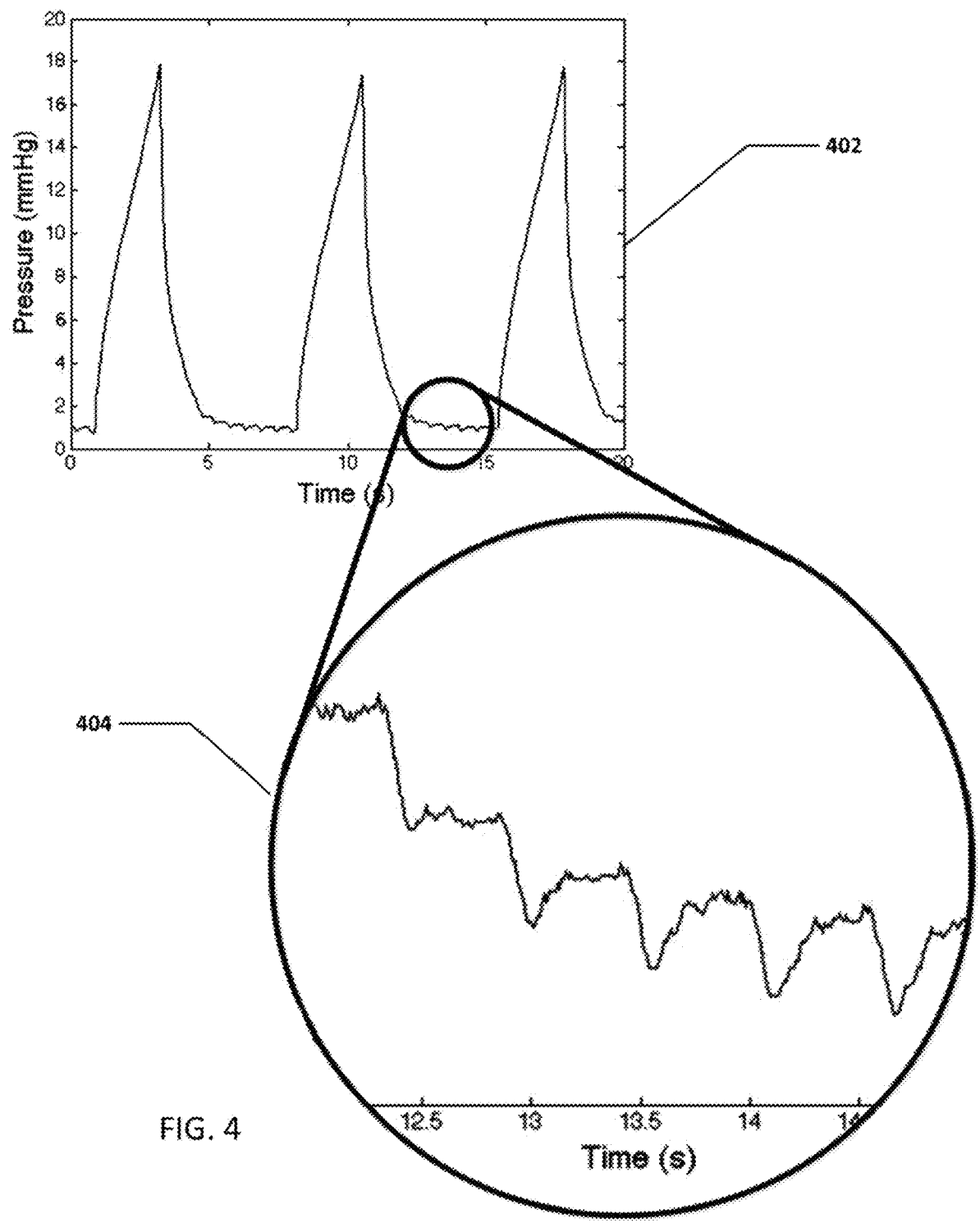
FIG. 4 is a graph showing pressure data from the ventilation tube of an animal.

FIG. 4 shows a detailed view of the pressure data between respirations shown in graph 402. Cardiogenic oscillations can be seen in detailed view 404 of pressure vs. time. The amplitude and or area under the curve for these pulses can be used as an indicator of relative cardiac output and/or pulmonary artery pressure. Not shown but also usefill in the same manner are cardiogenic oscillations in the flow signal.

Figure 5:
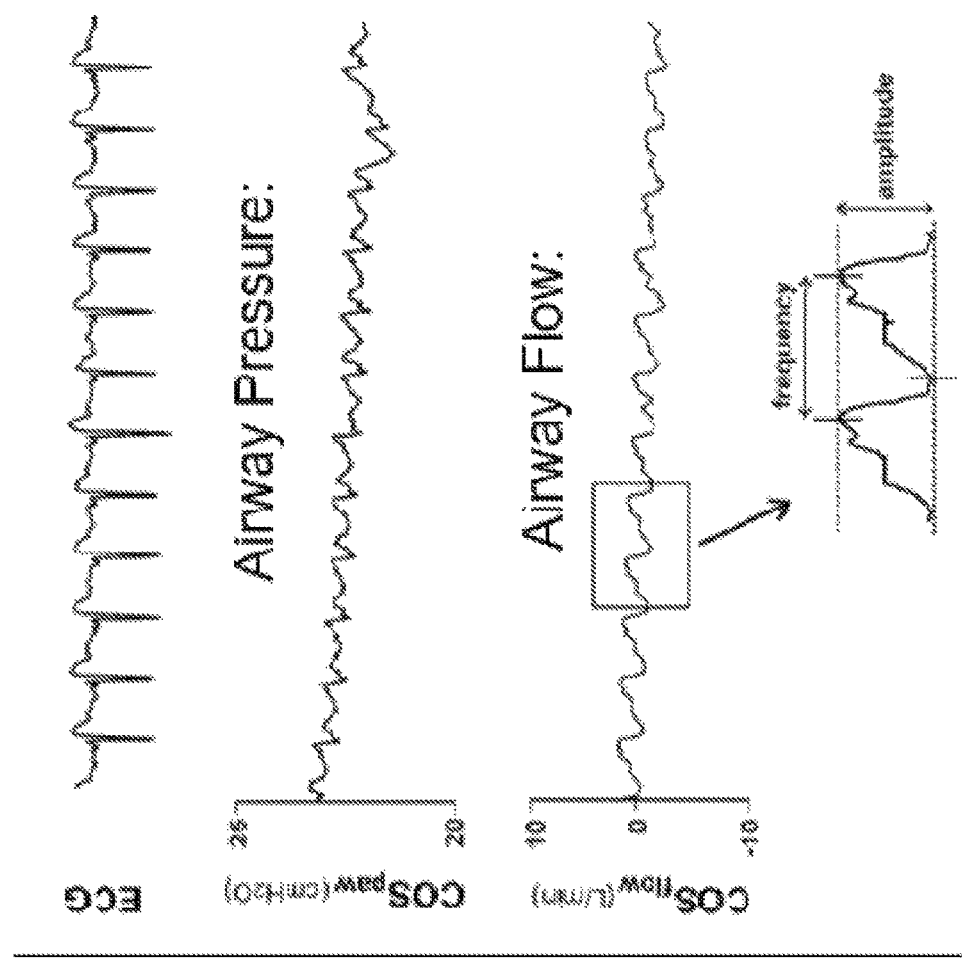
FIG. 5 shows a graph of the ECG curse as well as corresponding cardiogenic oscillations waveforms.

FIG. 5 shows a graph of the ECG curve, the cardiogenic oscillations waveform generated using data from pressure sensor(s), and the cardiogenic oscillations waveform generated using data from flow sensor(s) (from Turman, Gerardo, et al. "Pulmonary blood now generates cardiogenic oscillations." *Respiratory physiology & neurobiology* 167.3 (2009): 247-254.)

Also shown are the amplitude and the frequency of a cardiogenic oscillations waveform.

Figure 6:
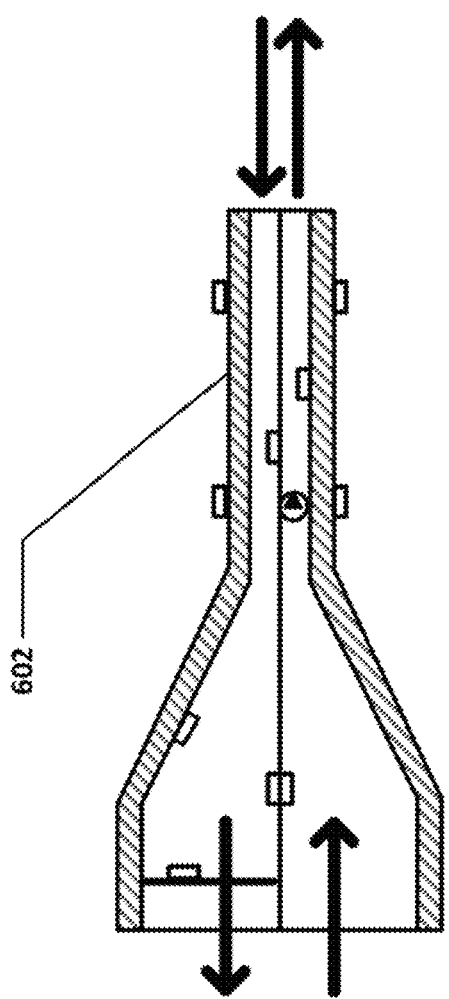
FIG. 6 shows an embodiment of the airway device/controller.

FIG. 6 shows another embodiment of the airway device. The neck portion 602 is extended so that it also serves as the mouthpiece portion, which is more straw-like than the previously shown embodiment.

Figure 7:
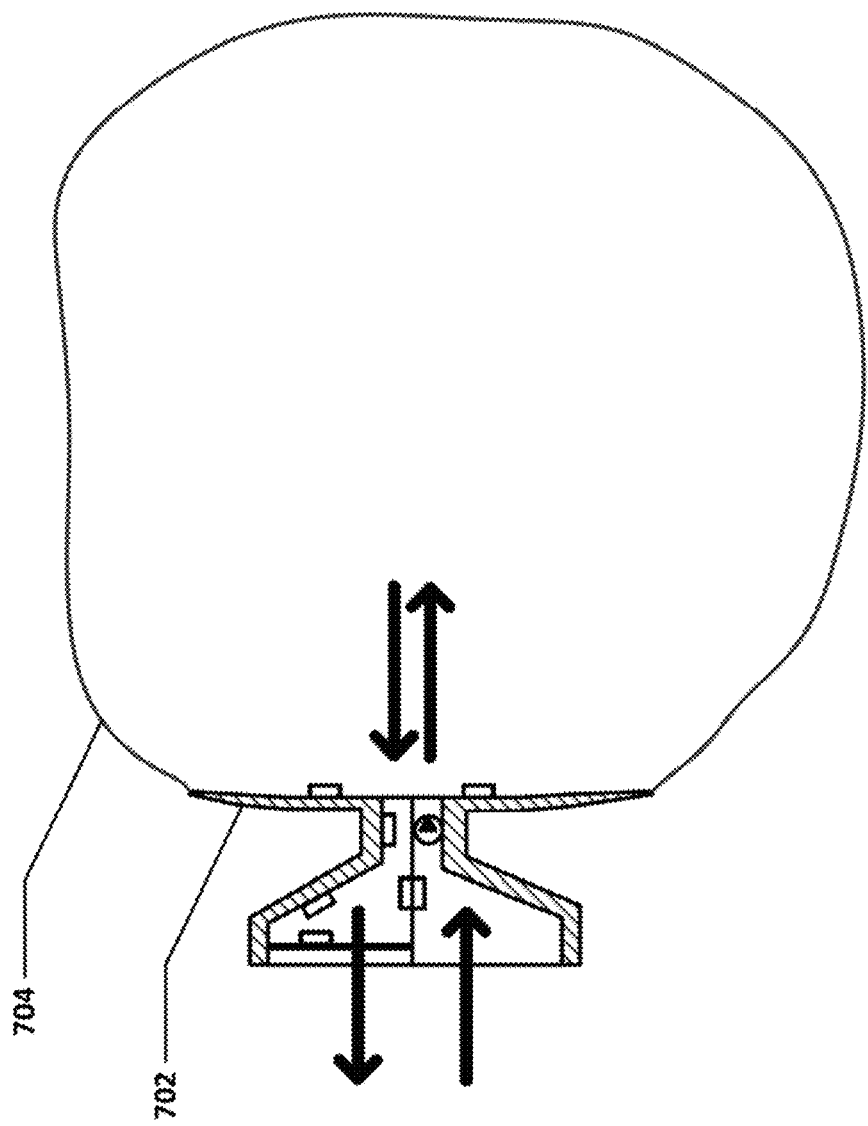
FIG. 7 shows an embodiment of the airway device/controller.

FIG. 7 shows another embodiment of the airway device. Mouthpiece area 702 is flat and designed to go over the lips/mouth. Strap 704 may hold the device on the face of the subject.

Figure 8:
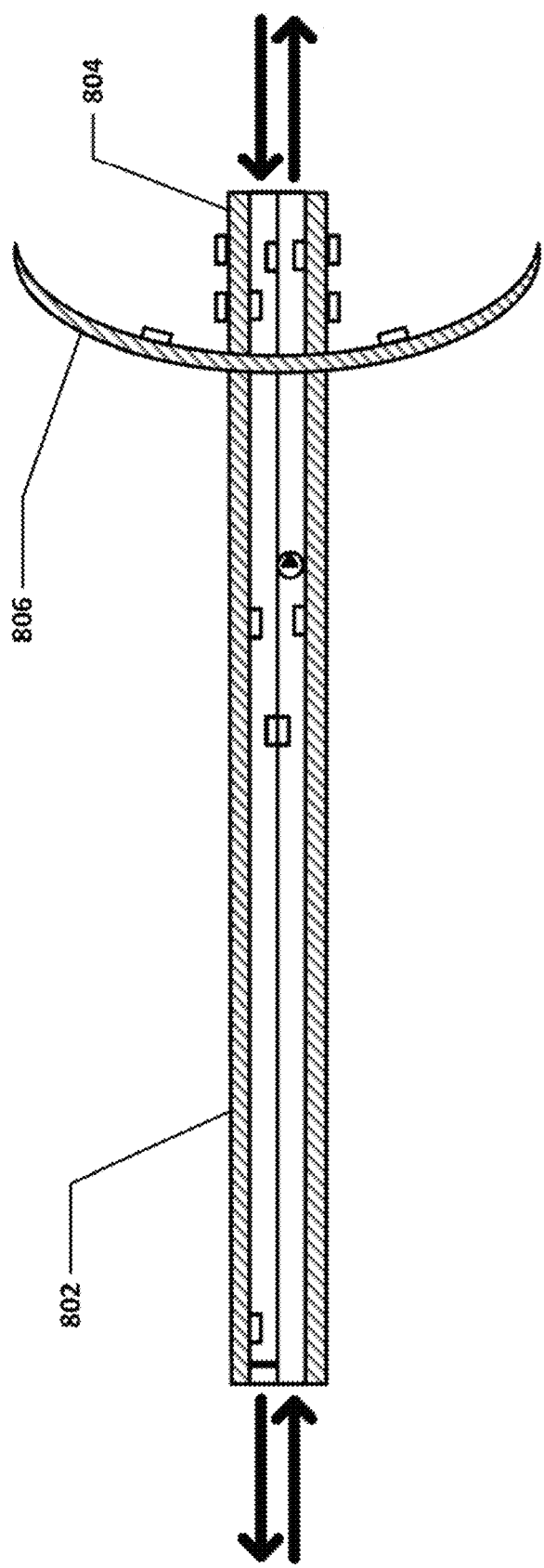
FIG. 8 shows an embodiment of the airway device/controller.

FIG. 8 shows another embodiment of the airway device. External opening section 802 of this embodiment is elongated and more narrow than previously shown embodiments. Section 802 may be flexible, as in flexible tubing, or may be rigid, or may be partially flexible and partially rigid. Mouthpiece section 804 includes mouth shield 806 to help keep the device in place. The various sensors and/or valves may be anywhere along the length of this embodiment.

FIG. 9 shows an embodiment of the airway device and controller where the controller is separate, at least in part, from the airway device. In this embodiment, controller 904 is a smart phone and communicates wirelessly with airway device 902, which may include a wireless data transmitter.

Figure 10:
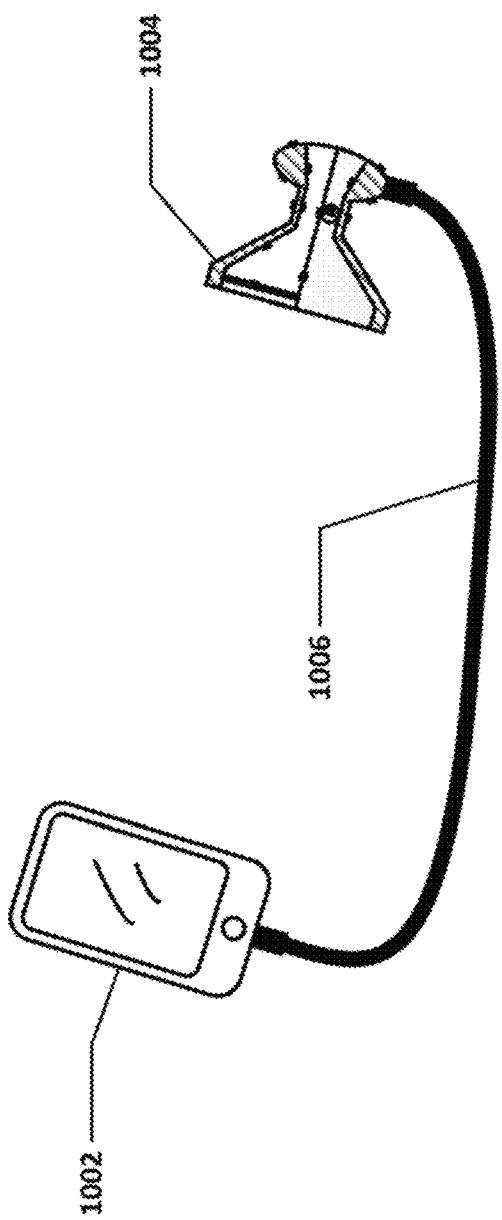
FIG. 10 shows an embodiment of the airway device connected to a controller in the form of a smart phone using a wired connection.

FIG. 10 shows an embodiment of the airway device and controller where the controller is separate, at least in part, from the airway device. In this embodiment, controller 1002 is a smart phone and communicates with airway device 1004 via a "wire" or cable 1006, for example, a USB cable. In this embodiment data may be collected and stored in airway device 1004 and periodically uploaded to controller 1002 via the cable.

The controller, whether it is separate from the airway device, or incorporated into the airway device, or some functions are located in the airway device and some located separately, may function as follows. The controller collects the data from the various sensors and analyzes them to determine cardiac output, stroke volume and/or cardiac function and/or other parameters. In addition, the controller may prompt the subject to help obtain the data from the sensors. For example, the controller may prompt the subject to hold his/her breath. The breath holding prompt may happen at certain phases of the breathing cycle, such as before or after inhalation and/or exhalation. The controller may prompt the subject to breath at a certain rate or to inhale, exhale, or hold his/her breath for a certain time period. Indicators may be present on the controller and/or the airway device to help the subject time certain activities. For example, the controller may prompt the subject to hold his/her breath until a light on the controller and/or airway device turns green, or until an auditory signal is heard.

The controller may also determine whether the data it is collecting is adequate for analysis. For example, if the subject's airway is closing between breaths, the data may be more difficult to analyze. The controller can sense when this is happening either by the pressure/flow profile or other parameters and can prompt the subject to adjust his/her breathing. For example, the controller may prompt the subject to breath more slowly, or to sit still. In addition, the controller may change the positive pressure of the airway device to help keep the airway open. Some possible prompts that the controller may provide to the subject are:

hold your breath for x seconds
hold your breath until the indicator does x
Breath normally until the indicator does x
exhale and then hold breath
inhale and then hold breath
breath normally
breath more slowly
Breath more quickly
Breath in slowly
Breath out slowly
Breath in quickly
Breath out quickly
testing is complete
begin exercising
end exercise Other prompts are also possible. The prompts may change depending on the data being collected. For example, if the controller determines that the airway is closing between breaths, the prompts may tell the subject to breathe differently, or the controller may cause the airway device to apply positive pressure to the airway. In addition, the user may be prompted at certain time(s) of the day to use the device, so that the device is used at the same time each day. For example, the device may prompt the user to use the device upon waking.

Other parameters that may be considered in determining whether the subject's breathing is optimal for data collection include: variability of peak-to-peak period and magnitude, waveform shape, etc.

The controller may analyze the data from the sensors to determine other conditions, including COPD, asthma, CHF, cancer, stroke, pulmonary embolism, dyspnea, paroxysmal, nocturnal dyspnea, emphysema, and any other condition that could have an impact on respiratory rate, temperature, stroke volume, heart rate, tidal volume, lung sounds, heart sounds, GI sounds, pO2, pCO2, pH, alcohol, urea, drugs, or any other of the monitored parameters.

Vagal tone/vasovagal syndrome may also be determined using the present invention. Slight changes in heart beat parameters, including amplitude, rate, waveform shape, etc., at different stages of the breathing cycle can be measured and vagal tone determined. For example, if the heart rate increases during inhalation, this may indicate a high vagal tone.

Example of Data Processing System

Figure 11:
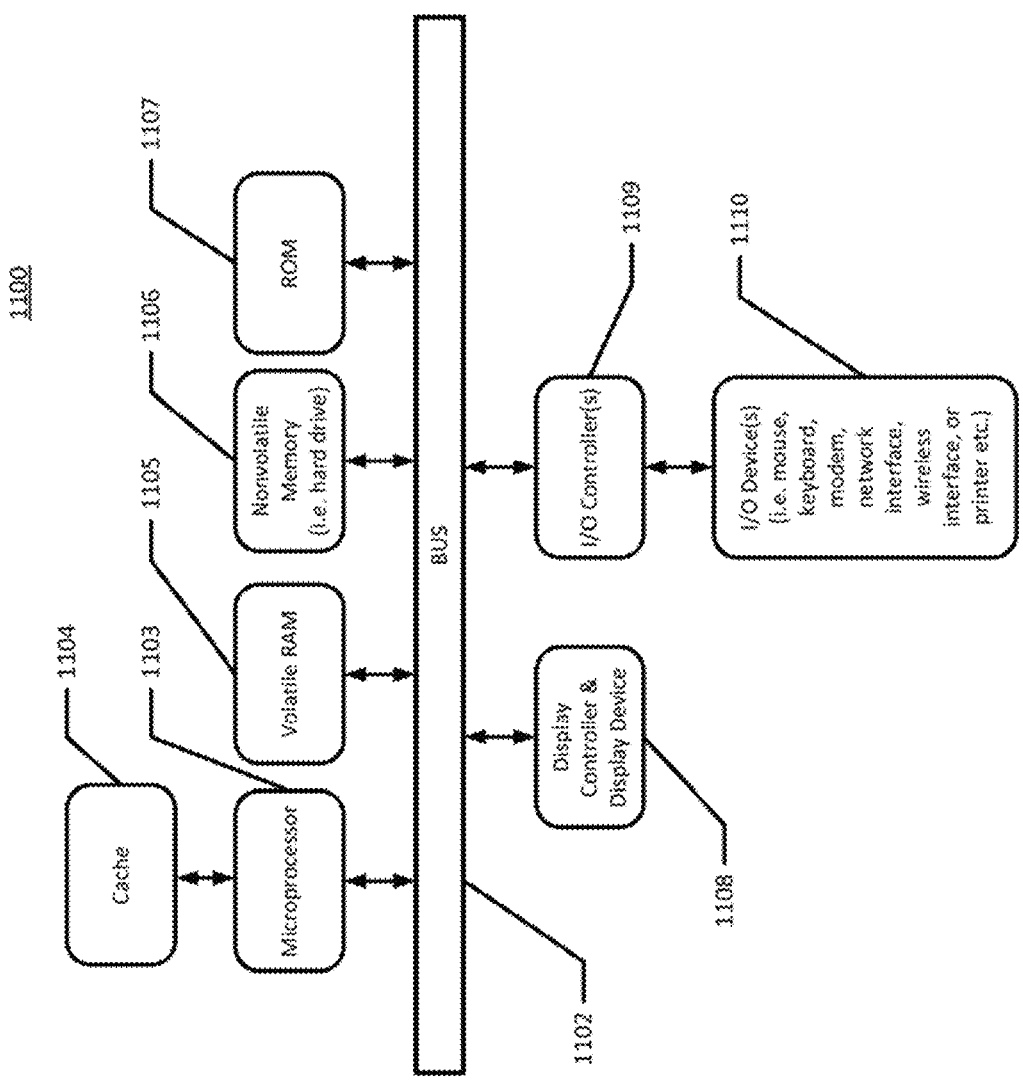
FIG. 11 is a block diagram of a data processing system, which may be used with any embodiments of the invention.

FIG. 11 is a block diagram of a data processing system, which may be used with any embodiment of the invention. For example, the system 1100 may be used as part of a controller. Note that while FIG. 11 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 11, the computer system 1100, which is a form of a data processing system, includes a bus or interconnect 1102 which is coupled to one or more microprocessors 1103 and a ROM 1107, a volatile RAM 1105, and a non-volatile memory 1106. The microprocessor 1103 is coupled to cache memory 1104. The bus 1102 interconnects these various components together and also interconnects these components 1103, 1107, 1105, and 1106 to a display controller and display device 1108, as well as to input/output (I/O) devices 1110, which may be mice, keyboards, modems, network interfaces, printers, and other devices which are well-known in the art.

Typically, the input/output devices 1110 are coupled to the system through input/output controllers 1109. The volatile RAM 1105 is typically implemented as dynamic RAM (DRAM) which requires power continuously in order to refresh or maintain the data in the memory. The non-volatile memory 1106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 11 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1102 may include one or more buses connected to each other through various bridges, controllers, and/or adapters, as is well-known in the art. In one embodiment, the I/O controller 1109 includes a USB (Universal Serial Bus) adapter for controlling USB peripherals. Alternatively, I/O controller 1109 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the figures herein may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Figure 12:
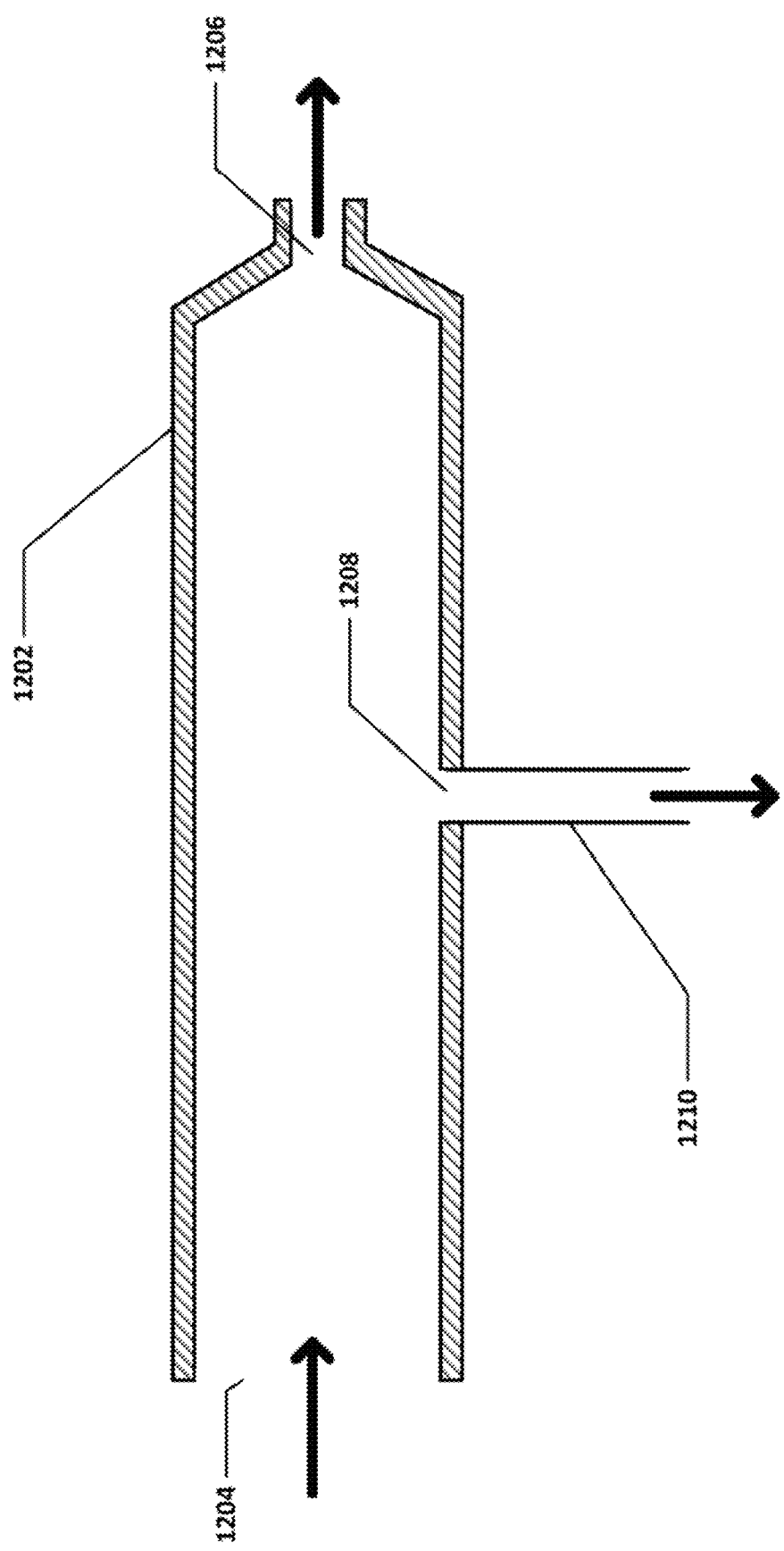
FIG. 12 shows an embodiment of a mouthpiece which includes a restrictor.

FIG. 12 shows an embodiment of an airway device which includes a restrictor. The restrictor helps reduce turbulent air flow within the airway device. Airway device 1202 in this embodiment has mouth opening 1204, which is larger than restrictor 1206. Restrictor 1206 is open to ambient air. As the user exhales into the airway device, restrictor 1206 restricts the airflow which increases the laminar nature of the air flow within the airway device. In this embodiment, as the user breathes through opening 1204, some air exits restrictor 1206, however some air, preferably air which is predominantly flowing in a laminar manner, exits sampling exit or lumen 1208. Sampling exit 1208 may connect directly to a pressure, or other, sensor, or it may connect to a pressure sensor or other sensor via connector 1210. The purpose of restrictor 1206 is to reduce turbulence in the air flow within the airway device so that the air exiting sampling exit 1208 is as laminar as possible. Note that this figure is showing an exhalation lumen only. A separate inhalation lumen may be incorporated into the device and/or the subject may be asked to inhale separately, either through his/her nose, or by removing the device from his/her mouth. Alternatively, the patient may also use the exhalation lumen for inhalation.

Figure 13:
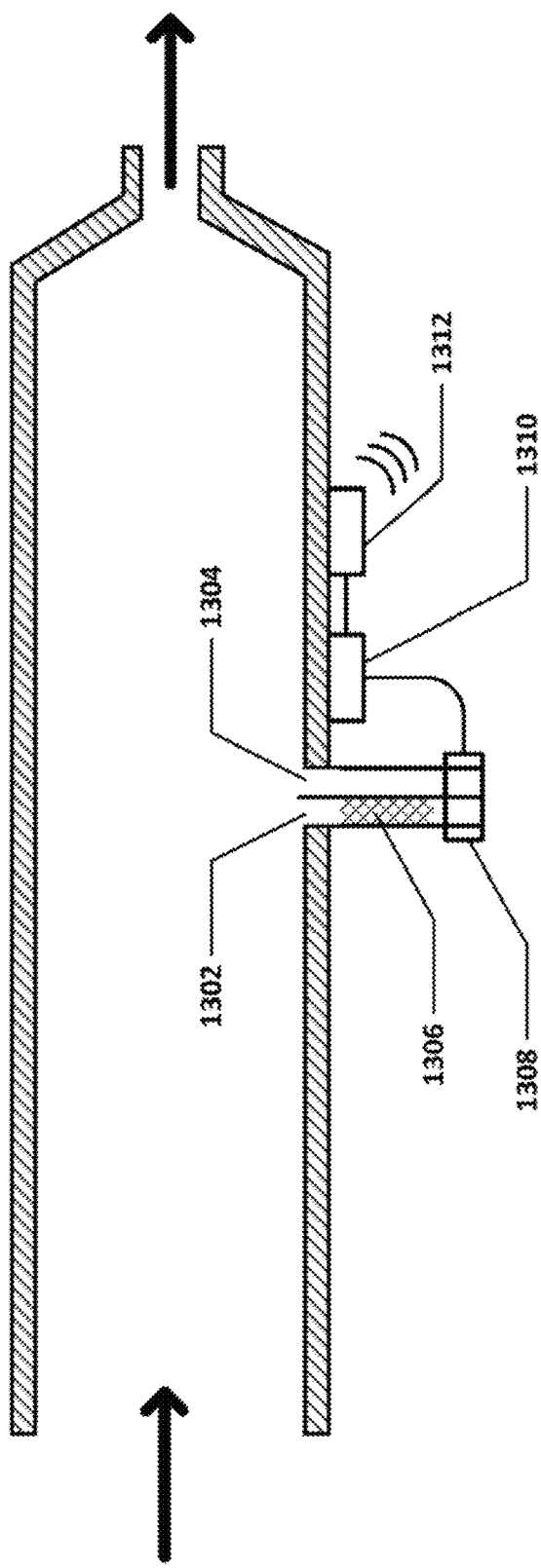
FIG. 13 shows an embodiment of a mouthpiece which incorporates a mechanical filter.

FIG. 13 shows an embodiment of an airway device which incorporates a mechanical filter. In this embodiment there are at least two sampling lumens, 1302 and 1304. One of the sampling lumen includes mechanical low pass filter 1306. The pressure sensor in this embodiment is a differential pressure sensor. Differential pressure sensor 1308 is in fluid communication with at least two sampling lumens or inputs, and compares the pressure reading between the two lumens. This configuration produces a cleaner pressure signal for analysis by circuit board 1310 by filtering out the pressure from the breaths and leaving those from the cardiogenic oscillations. Circuit board 1310 may be incorporated into the airway device or may be separate, for example on a separate controller, and communicated with either wirelessly or via wire. In this embodiment, the circuit board is incorporated into the airway device and communicates with a controller via wireless transmitter 1312. In this embodiment, circuit board 1310 and wireless transmitter 1312 may be considered to be part of the controller as well, for purposes of defining the controller. Filter 1306 may be made out of any suitable material including foam or any membrane that is semi-permeable to air. Note that this figure is showing an exhalation lumen only. A separate inhalation lumen may be incorporated into the device and/or the subject may be asked to inhale separately, either through his/her nose, or by removing the device from his/her mouth. Alternatively, the patient may also use the exhalation lumen for inhalation.

The mechanical low-pass filter isolates the lower frequency signals associated with natural breathing, which are subtracted from the signal leaving only the higher frequency cardiac oscillation signal. This filter may employ a partially-impermeable barrier between differential sensing and reference inputs. The high-frequency cardiac oscillation signal is seen by the sensing input, whereas the pressure changes due to breathing are low frequency enough to equilibrate across the membrane and are detected at both inputs. By breathing into the device with a slight expiratory pause, the COS signal can be reliably captured. Some embodiments may incorporate an additional, less sensitive, pressure sensor to monitor the entire breathing cycle and provide feedback to the patient about the size and frequency of the breaths, improving repeatability between measurements.

Figure 14:
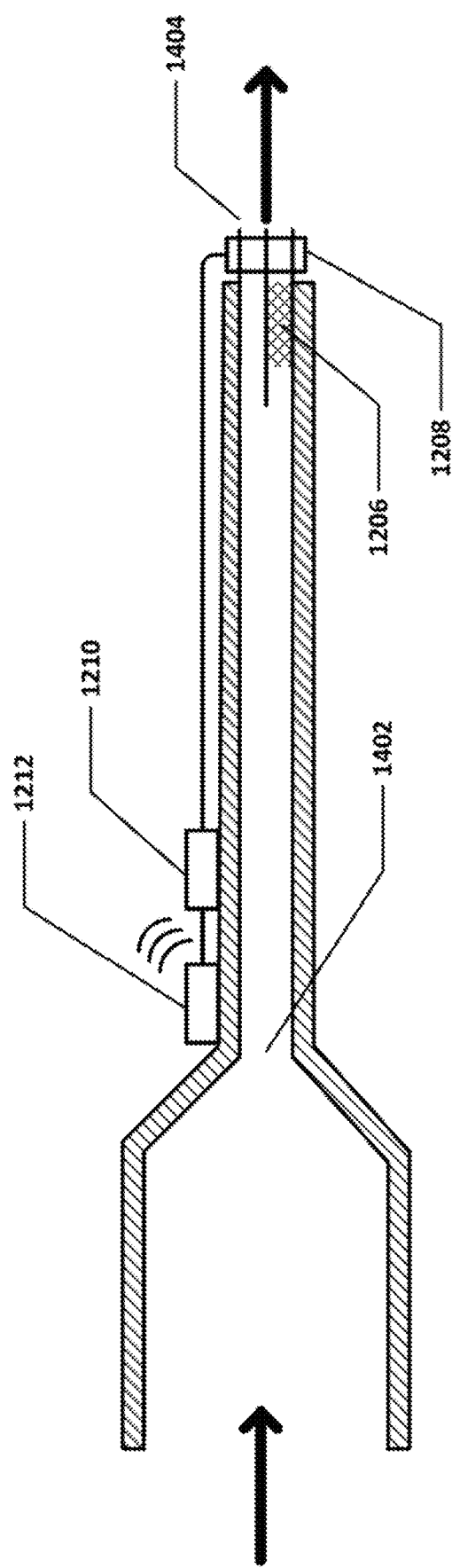
FIG. 14 shows an embodiment in which the restrictor and the sampling exit are combined

FIG. 14 shows an embodiment in which the restrictor and the sampling exit are combined. Restrictor 1402 reduces the turbulence in the airflow as air is breathed in and out of the airway device. Breathed air exits and may enter via outlet 1404. Differential pressure sensor 1308 may allow air to flow through it or alongside it to exit the airway device, or alternatively, the airway device may have an additional air exit (not shown). Note that this figure is showing an exhalation lumen only. A separate inhalation lumen may be incorporated into the device and/or the subject may be asked to inhale separately, either through his/her nose, or by removing the device from his/her mouth.

Note that the restrictor could be anything suitable, such as a flow control valve, a pressure control valve, etc.

Figure 15:
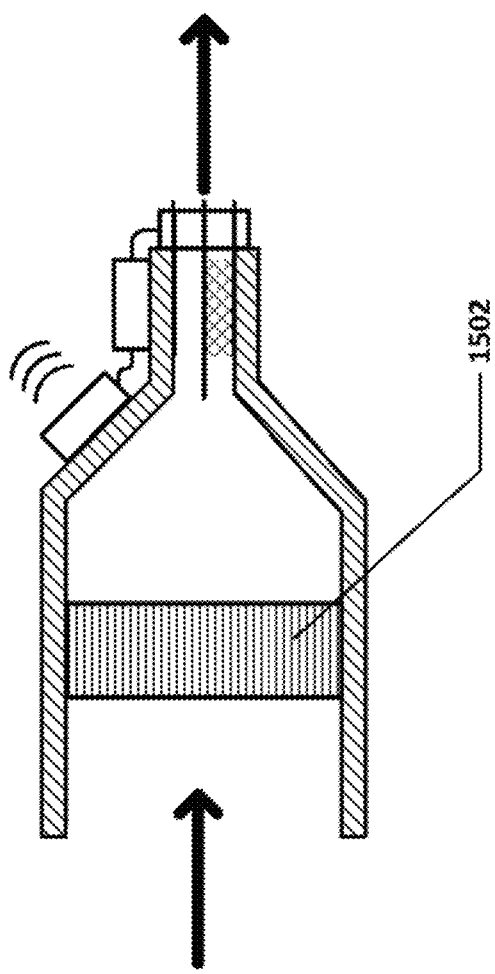
FIG. 15 shows an embodiment which incorporates a flow filter.

FIG. 15 shows an embodiment which incorporates a flow filter. Flow filter 1502 decreases the turbulence of the airflow coming into the airway device. In this embodiment, flow filter 1502 is used instead of a restrictor. The airway device may have an additional air exit (not shown). Flow filter 1502 may be made out of any suitable material such as polymer and in any suitable configuration such as a honeycomb or parallel capillary configuration. Note that this figure is showing an exhalation lumen only. A separate inhalation lumen may be incorporated into the device and/or the subject may be asked to inhale separately, either through his/her nose, or by removing the device from his/her mouth.

Any of the embodiments herein can be adapted to be used inside the mouth, or partially inside the mouth. For example, an airway device deeper inside the mouth may be advantageous in keeping the airway open for cleaner pressure measurements. Furthermore, any of the embodiments herein may also be adapted to be used with patients who are tracheally intubated, in which ease the devices described are attached to or in-line with the tracheal tube.

Figure 16:
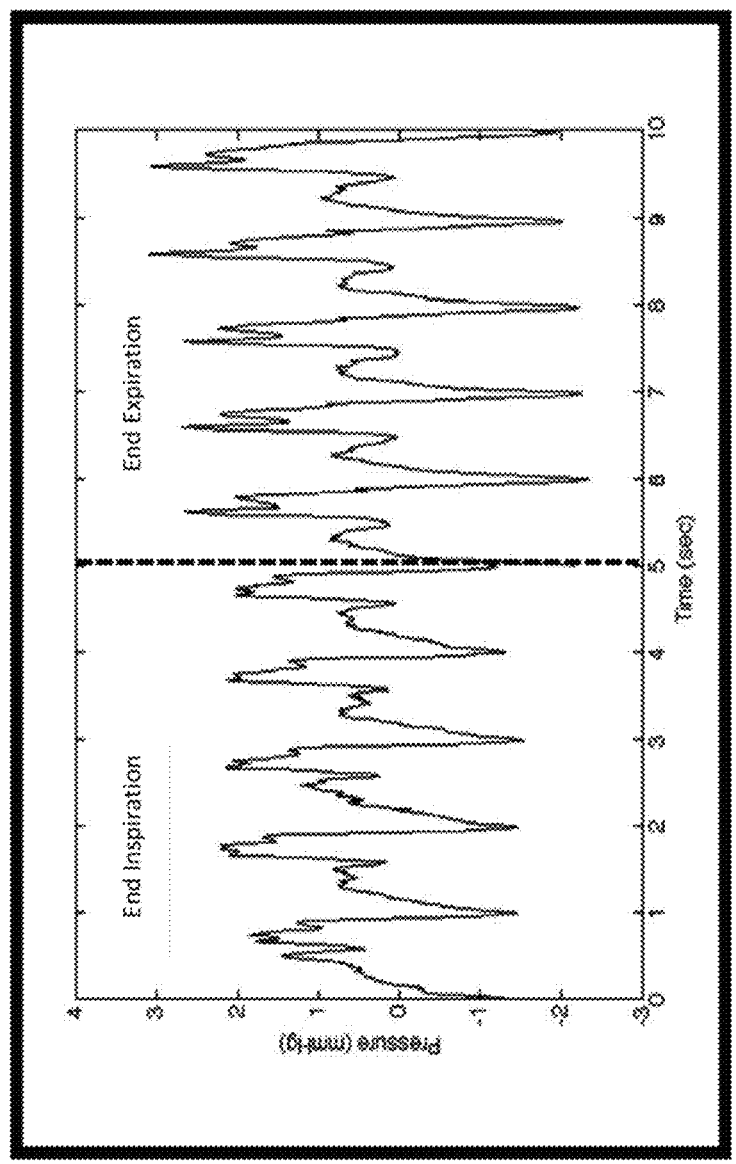
FIG. 16 shows a graph which demonstrates pulse pressure variability.

FIG. 16 shows a graph which demonstrates pulse pressure variability. As mentioned earlier, variability in the respiratory pulse pressure waveform can be used to determine hydration status, as well as volume status, and also pulmonary artery compliance. The graph in FIG. 16 shows the pulse pressure at end inspiration and at end expiration. Pulse pressure is defined as the difference between the systolic and diastolic pressure readings, or the amplitude of the waveform (lowest point to highest point). The difference in amplitude between these two waveforms is the pulse pressure variability. A large variability may indicate dehydration, where a decrease in variability over time may be an indicator that hydration is being restored or has been restored.

Figure 17:
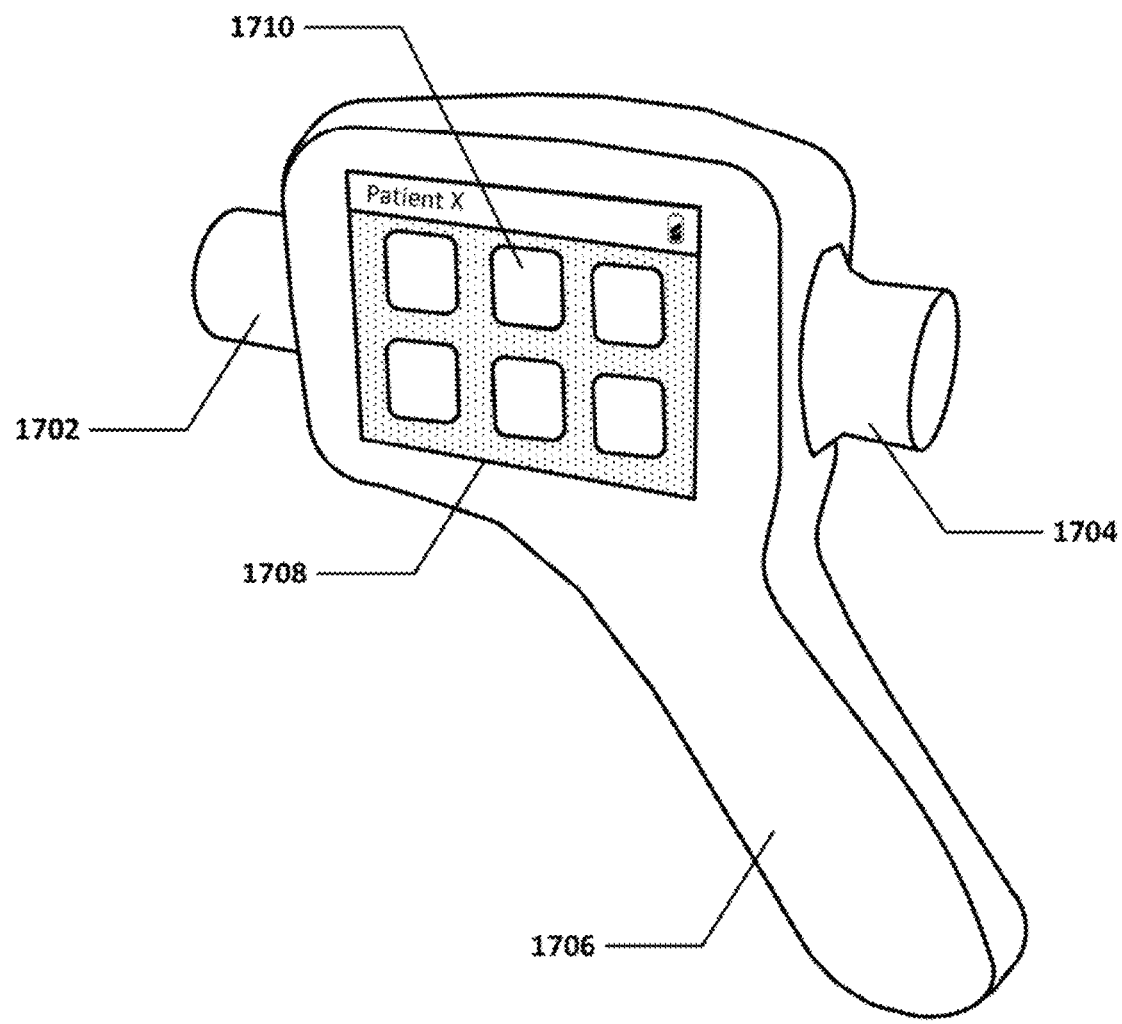
FIG. 17 shows an embodiment of the airway device/controller which includes a hand piece and at least some of the controller functions.

FIG. 17 shows an embodiment of the airway device/controller which includes a hand piece and at least some of the controller functions. The airway device of this embodiment includes 2 mouthpieces 1702 and 1704. The user breaths into one of these mouthpieces and breath exits through the other mouthpiece. Hand piece 1706 is held by the user or by the user's physician. Display 1708 displays one or more display areas 1710. These display areas may include buttons, or links, to more information, such as settings, waveforms, including waveforms showing HR (heart rate), SV (stroke volume), CO (cardiac output), PAC (pulmonary arterial compliance, etc., analytical results of waveform analysis, triggers for alarms/notices, etc. The airway device: controller of this embodiment may communicate wirelessly, or in a wired manner with one or more mobile devices, computers, servers, etc.

Figure 18:
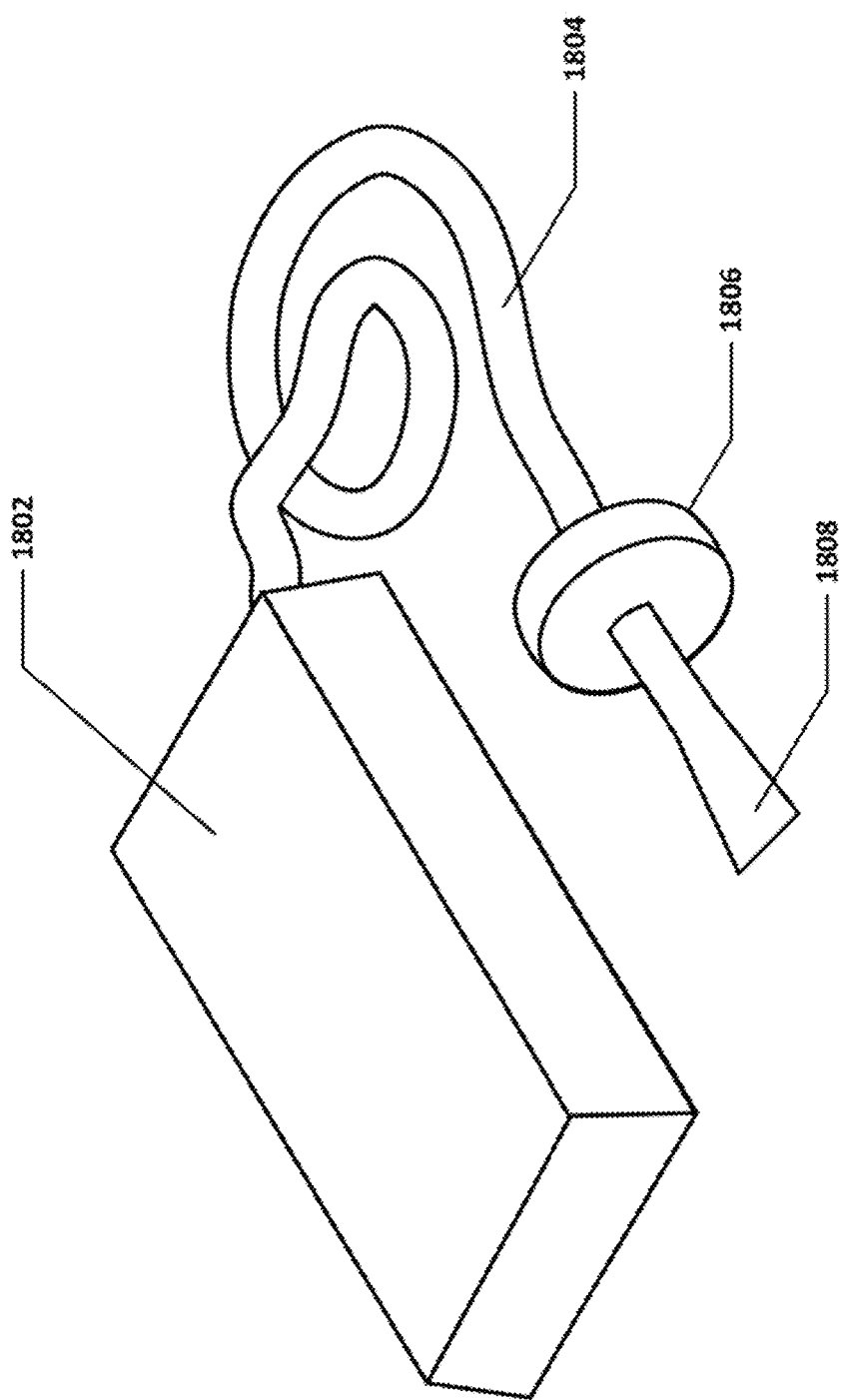
FIG. 18 shows another embodiment of the airway device/controller.

FIG. 18 shows another embodiment of the airway device/controller. This embodiment includes controller 1802, signal transmission tubing 1804, heat-moisture exchanger 1806 and mouthpiece 1808.

Embodiments of the airway device/controller may also, be incorporated with a standard or specialized inhaler, for example for asthma. The airway device/controller in these embodiments may include a feature which tracks usage of the airway device and/or inhaler to monitor use compliance.

Embodiments of the airway device/controller may include integration with electronic health records (EMR) or electronic health records or other systems. For example, data from the controller may be transmitted wirelessly (or wired) to a server in the internet which integrates the data with that of an EMR. The patient ID (possibly anonvmized) would be integrated into the metadata of the data transmitted by the controller so that the data would be integrated with the correct patient's medical record.

Data from multiple airway devices/controllers may be collected and aggregated and analyzed for trends. This data may be anonymized to comply with privacy rules.

In some embodiments of the airway device/controller, respiratory sinus arrhythmias (changes in heart rate due to breathing) may be tracked as an indicator of heart health or heart failure. Deviations from trends may be indicative of heart failure issues and may provide an alert. Because the data collected by the airway device may be continuous, for example, while the user sleeps, deviations from the norm (either for that patient or for a patient population) may indicate changes in health, and in particular, heart health.

In some embodiments of the airway device/controller, the device is used in an ambulatory manner. In other words, the user may use the device while walking around, watching TV, working, sleeping, resting, exercising or while performing everyday activities. The user is not tied to a stationary device, hospital nor clinic.

What is claimed is:

1. A system for determining one or more physiologic parameters of a subject, comprising:
   a flow or pressure sensor configured to monitor respiratory activity of the subject;
   a controller in communication with the flow or pressure sensor, wherein the controller is programmed to:
   extract one or more cardiogenic oscillation waveforms from the respiratory activity,
   determine shape data of the one or more cardiogenic oscillation waveforms to determine one or more physiologic parameters of the subject,
   provide an indication of a health status of the subject based on the determined one or more physiologic parameters,
   determine whether the one or more cardiogenic oscillation waveforms are insufficient for data analysis, based on airway closing between breaths, in determining the shape data, and
   prompt the subject to actively modify a speed of a breath of the subject to reduce an effect of respiratory activity on the one or more cardiogenic oscillation waveforms.

2. The system of claim 1 further comprising an airway device configured for positioning within a mouth of the subject.

3. The system of claim 2 wherein the controller is incorporated into the airway device.

4. The system of claim 2 wherein the airway device comprises a mouthpiece having one or more airway lumens defined through the airway device.

5. The system of claim 2 wherein the airway device is configured to incorporate a spirometry function.

6. The system of claim 2 wherein the airway device further comprises a restrictor which inhibits airflow such that laminar air flow is encouraged within the airway device.

7. The system of claim 2 further comprising a sensor configured to determine an additional parameter from the subject, wherein the additional parameter is selected from the group consisting of temperature, pH, and ECG.

8. The system of claim 1 wherein the one or more physiologic parameters is selected from the group consisting of airway pressure, airway flow, respiratory rate, stroke volume, heart rate, tidal volume, pO2, pCO2, pulse rate, and pulse pressure.

9. The system of claim 1 wherein the controller is incorporated into a remote device in wireless communication with the flow or pressure sensor.

10. The system of claim 9 wherein the remote device comprises a computer or smartphone.

11. The system of claim 1 wherein the controller is programmed to correlate a QRS complex peak obtained from ECG data of the subject with a corresponding valley in airway pressure in extracting one or more cardiogenic oscillation waveforms from the respiratory activity.

12. The system of claim 1 wherein the controller is programmed to determine an area under the one or more cardiogenic oscillation waveforms to determine relative cardiac output or pulmonary artery pressure.

13. The system of claim 1 wherein the controller is programmed to determine the one or more physiologic parameters comprising heart rate, or stroke volume.

14. The system of claim 1 wherein the controller is programmed to determine the one or more physiologic parameters comprising cardiac output.

15. The system of claim 1 wherein the controller is programmed to determine the one or more physiologic parameters comprising pulmonary arterial compliance.

16. The system of claim 1 further comprising a filter in communication with the flow or pressure sensor, wherein the filter is configured to isolate relatively higher frequency cardiac oscillation waveforms from relatively lower frequency pressure waveforms associated with natural breathing of the subject.

17. The system of claim 1 wherein the shape data comprises curve amplitude.

18. The system of claim 1 wherein the shape data comprises variations in the one or more cardiogenic oscillation waveforms.

19. The system of claim 1 wherein the controller is further programmed to determine variability in respiratory pulse pressure to determine hydration status, volume status, and pulmonary artery compliance of the subject.

20. The system of claim 1 wherein the system is configured to be portable.

21. The system of claim 1 wherein the system is configured for use with the subject when conscious.

22. A method of determining one or more physiologic parameters of a subject, comprising:

receiving flow or pressure data related to respiratory activity of the subject;

extracting one or more cardiogenic oscillation waveforms from the flow or pressure data; determining shape data of the one or more cardiogenic oscillation waveforms;

determining one or more physiologic parameters based on the determined shape data;

providing a health status to the subject based on the determined one or more physiologic parameters;

determining whether the one or more cardiogenic oscillation waveforms are insufficient for data analysis, based on airway closing between breaths, in determining the shape data; and prompting the subject to actively modify a speed of a breath of the subject to reduce an effect of respiratory activity on the one or more cardiogenic oscillation waveforms.

23. The method of claim 22 wherein receiving flow or pressure data comprises obtaining the flow or pressure data via an airway device positioned within a mouth of the subject.

24. The method of claim 23 further comprising determining additional physiologic parameters via the airway device, the additional physiologic parameter selected from the group consisting of airway pressure, airway flow, temperature, respiratory rate, stroke volume, heart rate, tidal volume, pO2, pCO2, pH, ECG, pulse rate, and pulse pressure.

25. The method of claim 23 wherein the airway device comprises mouthpiece having one or more airway lumens defined through the device.

26. The method of claim 23 wherein the airway device is configured to incorporate a spirometry function.

27. The method of claim 23 further comprising restricting airflow through the airway device such that laminar air flow is encouraged within the airway device.

28. The method of claim 22 wherein the one or more cardiogenic oscillation waveforms is extracted from the flow or pressure data via a controller.

29. The method of claim 28 wherein the controller is incorporated into a remote device in wireless communication.

30. The method of claim 29 wherein the remote device comprises a computer or smartphone.

31. The method of claim 28 wherein the controller is programmed to correlate a QRS complex peak obtained from ECG data of the subject with a corresponding valley in airway pressure in extracting one or more cardiogenic oscillation waveforms from the respiratory activity.

32. The method of claim 28 wherein the controller is programmed to determine an area under the one or more cardiogenic oscillation waveforms to determine relative cardiac output or pulmonary artery pressure.

33. The method of claim 22 further comprising determining additional physiologic parameters comprising heart rate, stroke volume, cardiac output, or pulmonary arterial compliance.

34. The method of claim 22 wherein receiving flow or pressure data further comprises filtering the flow or pressure data to isolate relatively higher frequency cardiac oscillation waveforms from relatively lower frequency pressure waveforms associated with natural breathing of the subject.

35. The method of claim 22 wherein determining shape data comprises determining curve amplitude or variations in the one or more cardiogenic oscillation waveforms.

36. The method of claim 22 wherein determining one or more physiologic parameters further comprises determining variability in respiratory pulse pressure to determine hydration status, and volume status of the subject.

37. The method of claim 22 wherein determining one or more physiologic parameters further comprises determining variability in respiratory pulse pressure to determine pulmonary artery compliance of the subject.

38. The method of claim 22 wherein receiving flow or pressure data comprises receiving the data while the subject remains ambulatory.

39. The method of claim 22 wherein receiving flow or pressure data comprises receiving the data while the subject remains conscious.

* * * * *